United States Patent
DeSantis et al.

(10) Patent No.: US 10,920,219 B2
(45) Date of Patent: Feb. 16, 2021

(54) TAGMENTATION USING IMMOBILIZED TRANSPOSOMES WITH LINKERS

(71) Applicants: Illumina, Inc., San Diego, CA (US); Illumina Cambridge Limited, Saffron Walden (GB)

(72) Inventors: Grace DeSantis, San Diego, CA (US); Stephen M. Gross, San Diego, CA (US); Jian-Sen Li, San Diego, CA (US); Natalie Morrell, Saffron Walden (GB); Andrew Slatter, Saffron Walden (GB); Kevin Shen, San Diego, CA (US); Samantha Snow, San Diego, CA (US)

(73) Assignees: ILLUMINA, INC., San Diego, CA (US); ILLUMINA CAMBRIDGE LIMITED

( * ) Notice: Subject to any disclaimer, the term of this patent is extended or adjusted under 35 U.S.C. 154(b) by 299 days.

(21) Appl. No.: 15/900,717

(22) Filed: Feb. 20, 2018

(65) Prior Publication Data
US 2018/0245069 A1    Aug. 30, 2018

Related U.S. Application Data

(60) Provisional application No. 62/461,620, filed on Feb. 21, 2017.

(51) Int. Cl.
| | |
|---|---|
| C12N 15/10 | (2006.01) |
| C12N 11/06 | (2006.01) |
| C12Q 1/6869 | (2018.01) |
| C12Q 1/6806 | (2018.01) |

(52) U.S. Cl.
CPC .......... *C12N 15/1065* (2013.01); *C12N 11/06* (2013.01); *C12Q 1/6806* (2013.01); *C12Q 1/6869* (2013.01); *C12Y 207/07* (2013.01)

(58) Field of Classification Search
CPC .............................. C12N 15/106; C12N 11/06
See application file for complete search history.

(56) References Cited

U.S. PATENT DOCUMENTS

| | | | |
|---|---|---|---|
| 5,925,545 A | 7/1999 | Reznikoff et al. |
| 5,965,443 A | 10/1999 | Reznikoff et al. |
| 7,057,026 B2 | 6/2006 | Barnes et al. |
| 7,057,031 B2 | 6/2006 | Olejnik et al. |
| 7,083,980 B2 | 8/2006 | Reznikoff et al. |
| 7,211,414 B2 | 5/2007 | Hardin et al. |
| 7,315,019 B2 | 1/2008 | Turner et al. |
| 7,329,492 B2 | 2/2008 | Hardin et al. |

(Continued)

FOREIGN PATENT DOCUMENTS

| | | |
|---|---|---|
| EP | 2 527 438 A1 | 11/2012 |
| EP | 2 712 931 A1 | 4/2014 |

(Continued)

OTHER PUBLICATIONS

Bentley et al. 2008. Accurate whole human genome sequencing using reversible terminator chemistry. *Nature*, 456:53-59.

(Continued)

*Primary Examiner* — Jezia Riley
(74) *Attorney, Agent, or Firm* — McNeill Baur PLLC

(57) ABSTRACT

The present disclosure relates to methods, compositions, and kits for treating target nucleic acids, including methods and compositions for fragmenting and tagging nucleic acid (e.g., DNA) using transposome complexes bound to a solid support.

15 Claims, 12 Drawing Sheets

Specification includes a Sequence Listing.

(56) References Cited

U.S. PATENT DOCUMENTS

| | | | |
|---|---|---|---|
| 7,405,281 B2 | 7/2008 | Xu et al. |
| 7,547,530 B2 | 6/2009 | Olejnik et al. |
| 7,608,434 B2 | 10/2009 | Reznikoff et al. |
| 7,897,737 B2 | 3/2011 | Wu et al. |
| 7,964,352 B2 | 6/2011 | Wu et al. |
| 8,361,727 B2 | 1/2013 | Wu et al. |
| 9,080,211 B2 | 7/2015 | Grunenwald et al. |
| 9,085,801 B2 | 7/2015 | Grunenwald et al. |
| 9,115,396 B2 | 8/2015 | Grunenwald et al. |
| 9,683,230 B2 | 6/2017 | Gormley et al. |
| 2008/0108082 A1 | 5/2008 | Rank et al. |
| 2008/0280773 A1 | 11/2008 | Fedurco et al. |
| 2009/0026082 A1 | 1/2009 | Rothberg et al. |
| 2009/0127589 A1 | 5/2009 | Rothberg et al. |
| 2010/0120098 A1 | 5/2010 | Grunenwald et al. |
| 2010/0137143 A1 | 6/2010 | Rothberg et al. |
| 2010/0282617 A1 | 11/2010 | Rothberg et al. |
| 2012/0208705 A1 | 8/2012 | Steemers et al. |
| 2012/0208724 A1 | 8/2012 | Steemers et al. |
| 2012/0301925 A1 | 11/2012 | Belyaev |
| 2013/0143774 A1 | 6/2013 | Actis et al. |
| 2014/0093916 A1 | 4/2014 | Belyaev |
| 2014/0194324 A1 | 7/2014 | Gormley et al. |
| 2015/0087534 A1 | 3/2015 | Gormley et al. |
| 2015/0284714 A1 | 10/2015 | Gormley et al. |
| 2015/0368638 A1 | 12/2015 | Steemers et al. |

FOREIGN PATENT DOCUMENTS

| | | |
|---|---|---|
| WO | WO 91/06678 A1 | 5/1991 |
| WO | WO 95/23875 A1 | 9/1995 |
| WO | WO 01/09363 A1 | 2/2001 |
| WO | WO 2004/018497 A2 | 3/2004 |
| WO | WO 2005/065814 A1 | 7/2005 |
| WO | WO 2007/123744 A2 | 11/2007 |
| WO | WO 2010/048605 A1 | 4/2010 |
| WO | WO 2012/061832 A1 | 5/2012 |
| WO | WO 2012/103545 A1 | 8/2012 |
| WO | WO 2012/106546 A2 | 8/2012 |
| WO | WO 2014/108810 A2 | 7/2014 |
| WO | WO 2015/002789 A1 | 1/2015 |
| WO | WO 2015/095226 A2 | 6/2015 |
| WO | WO 2015/160895 A2 | 10/2015 |
| WO | WO 2016/003814 A1 | 1/2016 |
| WO | WO 2016/037394 A1 | 3/2016 |
| WO | WO 2016/061517 A2 | 4/2016 |
| WO | WO 2016/130704 A2 | 8/2016 |
| WO | WO 2016/189331 A1 | 12/2016 |

OTHER PUBLICATIONS

Boeke et al. 1989. Transcription and reverse transcription of retrotransposons. *Ann. Rev. Microbiol.*, 43:403-434.

Brown et al. 1989. Retroviral integration: Structure of the initial covalent product and its precursor, and a role for the viral IN protein. *Proc. Natl. Acad. Sci. USA*, 86:2525-2529.

Colegio et al. 2001. In vitro transposition system for efficient generation of random mutants of *Campylobacter jejuni*. *Journal of Bacteriology*, 183(7):2384-2388.

Craig, N.L. 1996. Transposon Tn7. *Curr. Top. Microbiol. Immunol.*, 204:27-48.

Craig, N.L., 1996. V(D)J Recombination and transposition: Closer than expected. *Science*, 271:1512.

Deamer et al. 2000. Nanopores and nucleic acids: prospects for ultrarapid sequencing. *Trends Biotechnol.*, 18:147-151.

Deamer et al. 2002. Characterization of nucleic acids by nanopore analysis. *Acc. Chem. Res.*, 35(10):817-825.

Devine et al. 1994. Efficient integration of artificial transposons into plasmid targets in vitro: A useful tool for DNA mapping, sequencing and genetic analysis. Nucleic Acids Research, 22(18):3765-3772.

Gloor, G. B. 2004. Gene targeting in *Drosophila*. In W. J. Miller and P. Capy (Eds.), *Methods in Molecular Biology*, vol. 260, Chap. 8 (pp. 97-114). Totowa, NJ: Humana Press.

Goryshin et al. 1998. Tn5 in vitro transposition. *The Journal of Biological Chemistry*, 273(13):7367-7374.

Ichikawa, et al. 1990. In vitro transposition of Transposon Tn 3*. *The Journal of Biological Chemistry*, 265(31):18829-18832.

Kirby et al. 2002. Cryptic plasmids of Mycobacterium avium: Tn552 to the rescue, *Molecular Microbiology*, 43(1):173-186.

Kleckner et al. 1996. Tn10 and IS10 transposition and chromosome rearrangements: Mechanism and regulation in Vivo and in Vitro, *Curr Top Microbiol Immunol.*, 204:49-82.

Lampe et al. 1996. A purified *mariner* transposase is sufficient to mediate transposition in vitro, *The EMBO Journal*, 15(19):5470-5479.

Leriche et al. 2012. Cleavable linkers in chemical biology. *Bioorg. Med. Chem.*, 20(2):571-582.

Li et al. 2003. DNA molecules and configurations in a solid-state nanopore microscope. *Nat. Mater.*, 2:611-615.

Mizuuchi, K. 1983. In vitro transposition of bacteriophage Mu: A biochemical approach to a novel replication reaction. *Cell*, 35:785-794.

Ohtsubo et al. 1996. Bacterial insertion sequences. *Curr. Top. Microbiol. Immunol.*, 204:1-26.

Plasterk, R.H.A. 1996. The Tc1/*mariner* transposon family. *Curr. Topics Microbiol. Immunol.*, 204:125-143.

Reznikoff et al. 1999. Tn5: A molecular window on transposition. *Biochem. Biophys. Res. Commun.*, 266(3):729-734.

Savilahti, et al. 1995. The phage Mu transpososome core: DNA requirements for assembly and function. *The EMBO Journal*, 14:4893-4903.

Wilson et al. 2007. New transposon delivery plasmids for insertional metagenesis in *Bacillus anthracis*, J. Microbiol. Methods, 71(3):332-335.

Zhang et al. Epub Oct. 16, 2009. A novel mechanism of transposon-mediated gene activation. PLoS Genetics, 5(10):e1000689, pp. 1-9.

International Search Report and Written Opinion of the International Searching Authority dated May 2, 2018 for International Application No. PCT/US2018/018824 filed Feb. 20, 2018, 17 pages.

ns

SEQUENCE LISTING

```
<160> NUMBER OF SEQ ID NOS: 14

<210> SEQ ID NO 1
<211> LENGTH: 29
<212> TYPE: DNA
<213> ORGANISM: Artificial Sequence
<220> FEATURE:
<223> OTHER INFORMATION: P5 primer

<400> SEQUENCE: 1
aatgatacgg cgaccaccga gauctacac                                         29

<210> SEQ ID NO 2
<211> LENGTH: 24
<212> TYPE: DNA
<213> ORGANISM: Artificial Sequence
<220> FEATURE:
<223> OTHER INFORMATION: P7 primer

<400> SEQUENCE: 2
caagcagaag acggcatacg agat                                              24

<210> SEQ ID NO 3
<211> LENGTH: 33
<212> TYPE: DNA
<213> ORGANISM: Artificial Sequence
<220> FEATURE:
<223> OTHER INFORMATION: A14-ME adaptor sequence

<400> SEQUENCE: 3
tcgtcggcag cgtcagatgt gtataagaga cag                                    33

<210> SEQ ID NO 4
<211> LENGTH: 34
<212> TYPE: DNA
<213> ORGANISM: Artificial Sequence
<220> FEATURE:
<223> OTHER INFORMATION: B15-ME adaptor sequence

<400> SEQUENCE: 4
gtctcgtggg ctcggagatg tgtataagag acag                                   34

<210> SEQ ID NO 5
<211> LENGTH: 19
<212> TYPE: DNA
<213> ORGANISM: Artificial Sequence
<220> FEATURE:
<223> OTHER INFORMATION: ME' adaptor sequence

<400> SEQUENCE: 5
ctgtctctta tacacatct                                                    19

<210> SEQ ID NO 6
<211> LENGTH: 14
<212> TYPE: DNA
<213> ORGANISM: Artificial Sequence
<220> FEATURE:
```

<223> OTHER INFORMATION: A14 adaptor sequence

<400> SEQUENCE: 6
tcgtcggcag cgtc                                                           14

<210> SEQ ID NO 7
<211> LENGTH: 15
<212> TYPE: DNA
<213> ORGANISM: Artificial Sequence
<220> FEATURE:
<223> OTHER INFORMATION: B15 adaptor sequence

<400> SEQUENCE: 7
gtctcgtggg ctcgg                                                          15

<210> SEQ ID NO 8
<211> LENGTH: 19
<212> TYPE: DNA
<213> ORGANISM: Artificial Sequence
<220> FEATURE:
<223> OTHER INFORMATION: ME adaptor sequence

<400> SEQUENCE: 8
agatgtgtat aagagacag                                                      19

<210> SEQ ID NO 9
<211> LENGTH: 50
<212> TYPE: DNA
<213> ORGANISM: Artificial Sequence
<220> FEATURE:
<223> OTHER INFORMATION: Modified A14-ME #1

<400> SEQUENCE: 9
tttttttttt uuuacactcg tcggcagcgt cagatgtgta taagagacag                    50

<210> SEQ ID NO 10
<211> LENGTH: 38
<212> TYPE: DNA
<213> ORGANISM: Artificial Sequence
<220> FEATURE:
<223> OTHER INFORMATION: Modified A14-ME #2

<400> SEQUENCE: 10
ttuuutcgtc ggcagcgtca gatgtgtata agagacag                                 38

<210> SEQ ID NO 11
<211> LENGTH: 38
<212> TYPE: DNA
<213> ORGANISM: Artificial Sequence
<220> FEATURE:
<223> OTHER INFORMATION: Modified A14-ME #3

<400> SEQUENCE: 11
ttttutcgtc ggcagcgtca gatgtgtata agagacag                                 38

<210> SEQ ID NO 12
<211> LENGTH: 47
<212> TYPE: DNA
<213> ORGANISM: Artificial Sequence
<220> FEATURE:
<223> OTHER INFORMATION: Modified B15-ME #1

<400> SEQUENCE: 12
tttttttttt uuugtctcgt gggctcggag atgtgtataa gagacag                       47

```
<210> SEQ ID NO 13
<211> LENGTH: 39
<212> TYPE: DNA
<213> ORGANISM: Artificial Sequence
<220> FEATURE:
<223> OTHER INFORMATION: Modified B15-ME #2

<400> SEQUENCE: 13
ttuuugtctc gtgggctcgg agatgtgtat aagagacag                              39

<210> SEQ ID NO 14
<211> LENGTH: 39
<212> TYPE: DNA
<213> ORGANISM: Artificial Sequence
<220> FEATURE:
<223> OTHER INFORMATION: Modified B15-ME #3

<400> SEQUENCE: 14
ttttugtctc gtgggctcgg agatgtgtat aagagacag                              39
```

TAGMENTATION USING IMMOBILIZED TRANSPOSOMES WITH LINKERS

INCORPORATION BY REFERENCE TO ANY PRIORITY APPLICATIONS

The present application claims the benefit of priority to U.S. Provisional Patent Application No. 62/461,620, filed Feb. 21, 2017, which is hereby incorporated by reference in its entirety.

REFERENCE TO SEQUENCE LISTING

The present disclosure includes a sequence listing in Electronic format. The Sequence Listing is provided as a file entitled ILLINC-398A_Sequence_Listing.txt, created Feb. 20, 2017, which is approximately 3 KB in size. The information in the electronic format of the sequence listing is incorporated herein by reference in its entirety.

BACKGROUND

Field

The present disclosure relates to methods, compositions, and kits for treating nucleic acids, including methods and compositions for fragmenting and tagging nucleic acids (e.g., DNA) using transposome complexes immobilized on solid support.

Current protocols for next-generation sequencing (NGS) of nucleic acid samples routinely employ a sample preparation process that converts DNA or RNA into a library of fragmented, sequenceable templates. Sample preparation methods often require multiple steps and material transfers, and expensive instruments to effect fragmentation, and therefore are often difficult, tedious, expensive, and inefficient.

In one approach, nucleic acid fragment libraries may be prepared using a transposome-based method where two transposon end sequences, one linked to a tag sequence, and a transposase form a transposome complex. The transposome complexes are used to fragment and tag target nucleic acids in solution to generate a sequencer-ready tagmented library. The transposome complexes may be immobilized on a solid surface, such as through a biotin appended at the 5' end of one of the two end sequences. Use of immobilized transposomes provides significant advantages over solution-phase approaches by reducing hands-on and overall library preparation time, cost, and reagent requirements, lowering sample input requirements, and enabling the use of unpurified or degraded samples as a starting point for library preparation. Exemplary transposition procedures and systems for immobilization of transposomes on a solid surface to result in uniform fragment size and library yield are described in detail in WO2014/108810 and WO2016/189331, each of which is incorporated herein by reference in its entirety.

In certain bead-based tagmentation methods described in PCT Publ. No. WO2016/189331 and US 2014/093916A1, transposomes are bound to magnetic beads using biotin-streptavidin interactions. During the subsequent PCR amplification step of the protocol, biotin-streptavidin bonds are broken by thermal denaturation, thereby releasing the biotinylated tagmentation product into solution. Amplicons with sequences of interest, or target amplicons, can be enriched for example by hybridization capture if desired, and sequenced.

However, when libraries prepared by tagmentation using immobilized transposomes are enriched for certain regions of the genome using common hybridization capture methods, lower read enrichment may be achieved for certain regions in the genome, compared to, for example, enrichment of libraries generated using solution based transposome approaches.

In addition, the stability of the support-bound transposome complexes varies depending on the linker construct used to connect the transposome complex to the support. If complexes are removed from the support on storage or during library preparation, quality and efficiency of the resulting library is affected. Therefore, there is a need for immobilized transposome complexes with improved stability and associated methods that demonstrate improved efficiency of tagmented library production and, in turn, increased read enrichment for the resulting libraries. There is also a need for compositions and methods that will improve the read enrichment for the resulting libraries.

The present disclosure relates to support-bound transposome complexes with modified linkers and component arrangements. The present disclosure provides methods and compositions for producing sequencing-ready nucleic acid libraries using such modified complexes.

SUMMARY

The present disclosure relates to methods, compositions, and kits for treating nucleic acids, including methods and compositions for fragmenting and tagging DNA using transposome complexes on solid support.

The disclosure provides for a transposome complex comprising a transposase, a first transposon, and a second transposon, wherein the first transposon comprises (a) a 3' portion comprising a first transposon end sequence and (b) a first adaptor sequence at the 5' end of the first transposon end sequence, and the second transposon comprises a second transposon end sequence complementary to at least a portion of the first transposon end sequence. Typically, the first transposon end sequence and second transposon end sequence are annealed together, forming a double-stranded transposon end sequence that is recognized by a transposase, the combination of which forms a functional transposome complex.

In some aspects, the transposome complex comprises a cleavable linker that is capable of connecting the first transposon (and thus the complex) to the solid support. In such aspects, a first end of a cleavable linker is attached to the 5' end of the first adaptor sequence, and in some aspects, a second end of the cleavable linker is attached to an affinity element. The affinity element is capable of binding (covalently or non-covalently) to an affinity binding partner on a solid support. In some aspects, the affinity element is bound (covalently or non-covalently) to an affinity binding partner on the solid support, providing a solid support-bound transposome complex. These complexes are 5'-linker transposome complexes and solid support-bound 5'-linker transposome complexes.

In other aspects, the transposome complex comprises a 3' linker that is capable of connecting the second transposon (and thus the complex) to the solid support. In such aspects, a first end of the linker is attached to the 3' end of the second transposon and a second end of the linker is attached to an affinity element. The affinity element is capable of binding (covalently or non-covalently) to an affinity binding partner on a solid support. In some aspects, the affinity element is bound (covalently or non-covalently) to an affinity binding partner on the solid support, providing a solid support-bound transposome complex. In some aspects, the linker is a cleavable linker. These complexes are 3'-linker transposome complexes and solid support-bound 3'-linker transposome complexes.

In some aspects, the present disclosure relates to modified oligonucleotides. In some aspects, the modified oligonucleotide comprises a first transposon and a second transposon, wherein the first transposon comprises (a) a 3' portion comprising a first transposon end sequence and (b) a first adaptor sequence at the 5' end of the first transposon end sequence, and the second transposon comprises a second transposon end sequence complementary to at least a portion of the first transposon end sequence, and annealed thereto, and wherein a first end of a cleavable linker is attached to the 5' end of the first adaptor sequence and, in some aspects, a second end of the cleavable linker is attached to an affinity element.

In other aspects, the modified oligonucleotide comprises a first transposon and a second transposon, wherein the first transposon comprises (a) a 3' portion comprising a first transposon end sequence and (b) a first adaptor sequence at the 5' end of the first transposon end sequence, and the second transposon comprises a second transposon end sequence complementary to at least a portion of the first end sequence, and annealed thereto, and wherein a first end of a linker is attached to the 3' end of the second transposon and a second end of the linker is attached to an affinity element. In some aspects, the linker is a cleavable linker.

In some embodiments of the 3'-linker transposome complex, the affinity element and linker have a structure of Formula (I), (I'), (Ia), (Ib), (Ic), (I(a)), (I(b)), or (I(c)) as described herein. In some aspects, the affinity element is covalently linked to the 3' end of the second transposon, wherein the affinity element and linker have a structure of Formula (I):

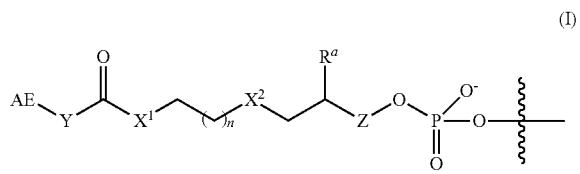

wherein:
AE is an affinity element;
Y is $C_{2-6}$alkylene;
$X^1$ is O, $NR^1$, or S;
wherein $R^1$ is H or $C_{1-10}$alkyl;
n is an integer selected from the group consisting of 1, 2, 3, 4, 5, and 6;
$X^2$ is O, $CH_2$, or S;
$R^a$ is H or —OH; and
Z is absent when $R^a$ is H, or is $CH_2$ when $R^a$ is H or OH;
wherein the ⁓ marks the connection point to the second transposon.

In some aspects, the linker described herein is a 5' linker, where the phosphate group in Formula (I) is a terminal phosphate group at the 5' position of the terminal nucleotide of the first transposon. In some aspects, the linker described herein is a 3' linker, where the phosphate group in Formula (I) is connected to a 3' hydroxyl of the second transposon oligonucleotide, such as the 3' terminal nucleotide.

In other aspects, the disclosure provides for methods of generating a library of tagged nucleic acid fragments from a double-stranded, target nucleic acid, comprising incubating the target with a transposome complex bound to a solid support as described herein. In some aspects, the methods comprise treating the target with the immobilized transposome complex under conditions wherein the target is fragmented and the 3' end the first transposon is joined to the 5' ends of the target fragments to produce a plurality of 5' tagged target fragments. In some embodiments, a plurality of transposome complexes is used.

In some embodiments, the methods further comprise amplifying one or more of the 5' tagged target fragments. In some embodiments, the methods further comprising sequencing one or more of the 5' tagged target fragments or amplification products thereof.

Thus, some additional embodiments of the present disclosure relate to a method of generating a library of tagged nucleic acid fragments, comprising:
  providing a solid support comprising a transposome complex described herein immobilized thereon; and
  contacting the solid support with a double-stranded, target nucleic acid under conditions sufficient to fragment the target nucleic acid into a plurality of target fragments, and to join the 3' end of the first transposon to the 5' ends of the target fragments to provide a plurality of 5' tagged target fragments.

In some aspects, the method further comprises amplifying the 5' tagged target fragments.

In some aspects, the disclosure provides for a library of 5' tagged target fragments produced by the methods described herein.

The disclosure further provides for methods of preparing modified oligonucleotides, transposome complexes, and solid support-bound transposome complexes as described herein. In some aspects, such methods comprise treating a transposase with the first and second transposons as described herein under conditions suitable for forming the complex. Methods for preparing a solid support-bound transposome complex comprise incubating a transposome complex as described herein with a solid support comprising an affinity binding partner under conditions sufficient for the affinity element to bind (covalently or non-covalently) with the affinity binding partner.

In some embodiments of the compositions and methods described herein, the transposome complexes comprise two populations, wherein the first adaptor sequences in each population are different.

DETAILED DESCRIPTION

Figure 1:
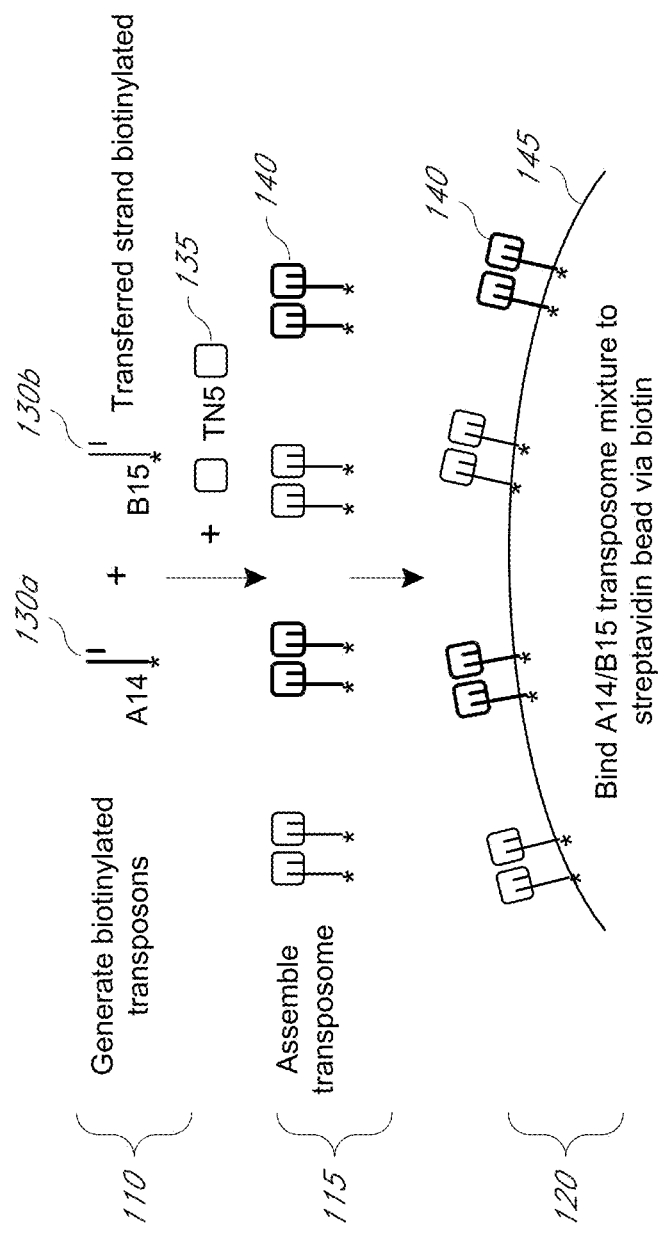
FIG. 1 illustrates exemplary steps of a method of affixing an embodiment of a transposome complex to a bead surface.

Libraries of fragmented nucleic acids are often created from genomic nucleic acids for use in next generation sequencing (NGS) applications. The present disclosure provides for methods, compositions, and kits for an immobilized transpositional library preparation method. The immobilized transpositional library preparation method is fast relative to other library preparation methods and is effective in preparing libraries from both gross or non-purified samples (such as blood, sputum, cellular extracts, and the like) and purified samples (such as purified genomic nucleic acids). Generally, a transposome is immobilized on a substrate, such as a slide or bead, using covalent or non-covalent binding partners, e.g., an affinity element and an affinity binding partner (FIG. 1). For example, a transposome complex is immobilized on a streptavidin-coated bead through a biotinylated linker attached to the transposome complex. The target nucleic acids are captured by the immobilized transposome complex and the nucleic acids are fragmented and tagged ("tagmentation"). The tagged fragments are amplified, amplicons of interest are optionally captured (e.g., via hybridization probes), and the tagged fragments are sequenced.

Figure 3:
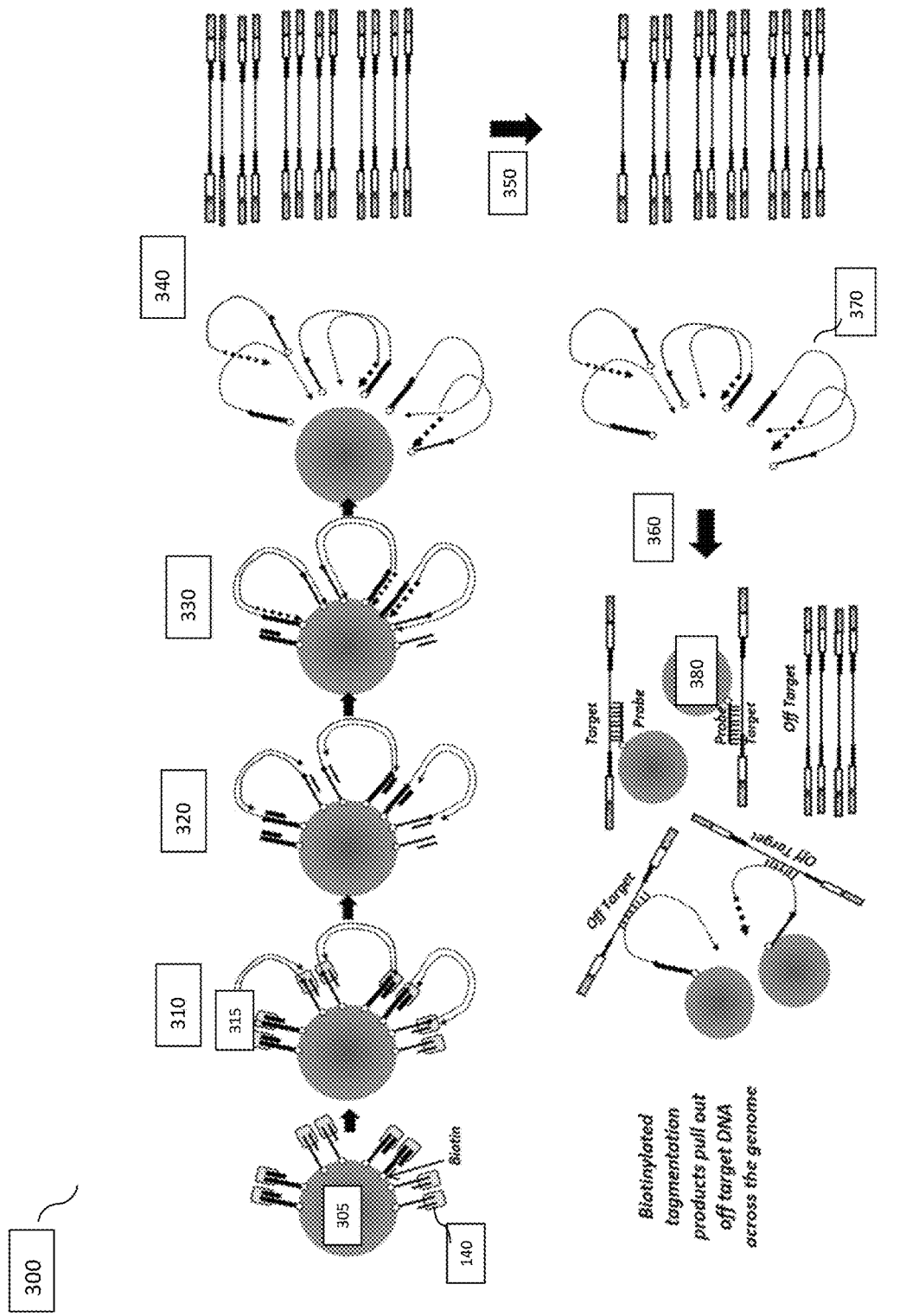
FIG. 3 shows exemplary steps of the method of fragmenting and tagging DNA using transposome complexes immobilized on a bead surface followed by target enrichment leading to contaminating off target reads.

Using solid support-linked transposome complexes for library preparation reduces the need for normalization of sample input going into the library preparation process and for normalization of library output before enrichment or sequencing steps. Using these complexes also produces libraries with more consistent insert sizes relative to solution-phase methods, even when varying sample input concentrations are used. However, it was observed that certain transposome complexes with biotinylated linkers have reduced stability. In addition, certain support-bound complex configurations produce off-target products; in particular, hybridization and capture of amplicons of 5' tagged target fragments may be contaminated by fragments of nucleic acids that are still hybridized with immobilized nucleic acids (FIG. 3). This inefficiency can result in the waste of reagents and sequencing instrument or flow cell space with off-target fragments and sequencing data. The present application discloses various transposome complex designs to address the library quality issues and reduce off-target capture, and complexes with modified linkers that demonstrate improved chemical stability.

In some embodiments, the nucleic acid libraries obtained by the methods disclosed herein can be sequenced using any suitable nucleic acid sequencing platform to determine the nucleic acid sequence of the target sequence. In some respects, sequences of interest are correlated with or associated with one or more congenital or inherited disorders, pathogenicity, antibiotic resistance, or genetic modifications. Sequencing may be used to determine the nucleic acid sequence of a short tandem repeat, single nucleotide polymorphism, gene, exon, coding region, exome, or portion thereof. As such, the methods and compositions described herein relate to creating sequenceable libraries useful in, but not limited to, cancer and disease diagnosis, prognosis and therapeutics, DNA fingerprinting applications (e.g., DNA databanking, criminal casework), metagenomic research and discovery, agrigenomic applications, and pathogen identification and monitoring.

The number of steps required to transform a target nucleic acid such as DNA into adaptor-modified templates ready for next generation sequencing can be minimized by the use of transposase-mediated fragmentation and tagging. This process, referred to herein as "tagmentation," often involves modification of a target nucleic acid by a transposome complex comprising a transposase enzyme complexed with a transposon pair comprising a single-stranded adaptor sequence and a double-stranded transposon end sequence region, along with optional additional sequences designed for a particular purpose. Tagmentation results in the simultaneous fragmentation of the target nucleic acid and ligation of the adaptors to the 5' ends of both strands of duplex nucleic acid fragments. Where the transposome complexes are support-bound, the resulting fragments are bound to the solid support following the tagmentation reaction (either directly in the case of the 5' linked transposome complexes, or via hybridization in the case of the 3' linked transposome complexes).

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

Chemical Terminology

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment, for example, physical adsorption.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —OCF3), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

In some embodiments, the transposome complexes are immobilized to a support via one or more polynucleotides (e.g., oligonucleotides), such as a polynucleotide (oligonucleotide) comprising a transposon end sequence. In some embodiments, the transposome complex may be immobilized via a linker appended to the end of a transposon sequence, for example, coupling the transposase enzyme to the solid support. In some embodiments, both the transposase enzyme and the transposon polynucleotide (e.g., oligonucleotide) are immobilized to the solid support. When referring to immobilization of molecules (e.g., nucleic acids, enzymes) to a solid support, the terms "immobilized", "affixed" and "attached" are used interchangeably herein and both terms are intended to encompass direct or indirect, covalent or non-covalent attachment, unless indicated otherwise, either explicitly or by context. In certain embodiments of the present disclosure covalent attachment may be preferred, but generally all that is required is that the molecules (e.g. nucleic acids, enzymes) remain immobilized or attached to the support under the conditions in which it is intended to use the support, for example in applications requiring nucleic acid amplification and/or sequencing. In some instances, in bead based tagmentation, transposomes may be bound to a bead surface via a ligand pair, e.g., an affinity element and affinity binding partner.

Transposomes and Transposases

Transposon based technology can be utilized for fragmenting DNA, for example, as exemplified in the workflow for NEXTERA™ XT and FLEX DNA sample preparation kits (Illumina, Inc.), wherein target nucleic acids, such as genomic DNA, are treated with transposome complexes that simultaneously fragment and tag ("tagmentation") the target, thereby creating a population of fragmented nucleic acid molecules tagged with unique adaptor sequences at the ends of the fragments.

A transposition reaction is a reaction wherein one or more transposons are inserted into target nucleic acids at random sites or almost random sites. Components in a transposition reaction include a transposase (or other enzyme capable of fragmenting and tagging a nucleic acid as described herein, such as an integrase) and a transposon element that includes a double-stranded transposon end sequence that binds to the enzyme, and an adaptor sequence attached to one of the two transposon end sequences. One strand of the double-stranded transposon end sequence is transferred to one strand of the target nucleic acid and the complementary transposon end sequence strand is not (i.e., a non-transferred transposon sequence). The adaptor sequence can comprise one or more functional sequences (e.g., primer sequences) as needed or desired.

A "transposome complex" is comprised of at least one transposase enzyme and a transposon recognition sequence. In some such systems, the transposase binds to a transposon recognition sequence to form a functional complex that is capable of catalyzing a transposition reaction. In some aspects, the transposon recognition sequence is a double-stranded transposon end sequence. The transposase, or integrase, binds to a transposase recognition site in a target nucleic acid and inserts the transposon recognition sequence into a target nucleic acid. In some such insertion events, one strand of the transposon recognition sequence (or end sequence) is transferred into the target nucleic acid, resulting also in a cleavage event. Exemplary transposition procedures and systems that can be readily adapted for use with the transposases of the present disclosure are described, for example, in PCT Publ. No. WO10/048605, U.S. Pat. Publ. No. 2012/0301925, U.S. Pat. Publ. No. 2012/13470087, or U.S. Pat. Publ. No. 2013/0143774, each of which is incorporated herein by reference in its entirety.

Exemplary transposases that can be used with certain embodiments provided herein include (or are encoded by): Tn5 transposase (see Reznikoff et al., *Biochem. Biophys. Res. Commun.* 2000, 266, 729-734), *Vibrio harveyi* (transposase characterized by Agilent and used in SureSelect QXT product), MuA transposase and a Mu transposase recognition site comprising R1 and R2 end sequences (Mizuuchi, K., Cell, 35: 785, 1983; Savilahti, H, et al., EMBO J., 14:4893, 1995), *Staphylococcus aureus* Tn552 (Colegio, O. et al., J. Bacteriol., 183:2384-8, 2001; Kirby, C. et al., Mol. Microbiol., 43:173-86, 2002), Ty1 (Devine & Boeke, Nucleic Acids Res., 22:3765-72, 1994 and PCT Publ. No. WO95/23875), Transposon Tn7 (Craig, N. L., Science, 271:1512, 1996; Craig, N. L., Curr. Top. Microbiol. Immunol., 204:27-48, 1996), Tn/O and IS10 (Kleckner N. et al., Curr. Top. Microbiol. Immunol., 204:49-82, 1996), Mariner transposase (Lampe, D. J. et al., EMBO J., 15:5470-9, 1996), Tc1 (Plasterk, R. H., Curr. Top. Microbiol. Immunol., 204:125-43, 1996), P Element (Gloor, G. B., Methods Mol. Biol., 260:97-114, 2004), Tn3 (Ichikawa & Ohtsubo, J. Biol. Chem., 265:18829-32, 1990), bacterial insertion sequences (Ohtsubo & Sekine, Curr. Top. Microbiol. Immunol. 204:1-26, 1996), retroviruses (Brown et al., Proc. Natl. Acad. Sci. USA, 86:2525-9, 1989), and retrotransposon of yeast (Boeke & Corces, Ann. Rev. Microbiol. 43:403-34, 1989). More examples include IS5, Tn10, Tn903, IS911, and engineered versions of transposase family enzymes (Zhang et al., (2009) PLoS Genet. 5:e1000689. Epub October 16; Wilson C. et al. (2007) J. Microbiol. Methods 71:332-5). The methods described herein could also include combinations of transposases, and not just a single transposase.

In some embodiments, the transposase is a Tn5, MuA, or *Vibrio harveyi* transposase, or an active mutant thereof. In other embodiments, the transposase is a Tn5 transposase or an active mutant thereof. In some embodiments, the Tn5 transposase is a hyperactive Tn5 transposase (see, e.g., Reznikoff et al., PCT Publ. No. WO2001/009363, U.S. Pat. Nos. 5,925,545, 5,965,443, 7,083,980, and 7,608,434, and Goryshin and Reznikoff, J. Biol. Chem. 273:7367, 1998), or an active mutant thereof. In some aspects, the Tn5 transposase is a Tn5 transposase as described in PCT Publ. No. WO2015/160895, which is incorporated herein by reference. In some embodiments, the Tn5 transposase is a fusion protein. In some embodiments, the Tn5 transposase fusion protein comprises a fused elongation factor Ts (Tsf) tag. In some embodiments, the Tn5 transposase is a hyperactive Tn5 transposase comprising mutations at amino acids 54, 56, and 372 relative to the wild type sequence. In some embodiments, the hyperactive Tn5 transposase is a fusion protein, optionally wherein the fused protein is elongation factor Ts (Tsf). In some embodiments, the recognition site is a Tn5-type transposase recognition site (Goryshin and Reznikoff, J. Biol. Chem., 273:7367, 1998). In one embodiment, a transposase recognition site that forms a complex with a hyperactive Tn5 transposase is used (e.g., EZ-Tn5™ Transposase, Epicentre Biotechnologies, Madison, Wis.).

In some embodiments, the transposome complex is a dimer of two molecules of a transposase. In some embodiments, the transposome complex is a homodimer, wherein two molecules of a transposase are each bound to first and second transposons of the same type (e.g., the sequences of the two transposons bound to each monomer are the same, forming a "homodimer"). In some embodiments, the compositions and methods described herein employ two populations of transposome complexes. In some embodiments, the transposases in each population are the same. In some embodiments, the transposome complexes in each population are homodimers, wherein the first population has a first adaptor sequence in each monomer and the second population has a different adaptor sequence in each monomer.

In some embodiments, the transposase is a Tn5 transposase. In some embodiments, the transposase complex comprises a transposase (e.g., a Tn5 transposase) dimer comprising a first and a second monomer. Each monomer comprises a first transposon and a second transposon, where the first transposon comprises a first transposon end sequence at its 3' end and an first adaptor sequence (where the adaptor sequences in each monomer of a dimer are the same or different), and the second transposon comprises a second transposon end sequence at least partially complementary to the first transposon end sequence. In some embodiments of the 5' cleavable linker aspect, the first transposon comprises at its 5' end a cleavable linker connected to an affinity element. In some embodiments of the 3' linker aspect, the second transposon comprises at its 3' end a linker (optionally cleavable) connected to an affinity element. Thus, in preferred embodiments, one transposon from each monomer comprises an affinity element. In some embodiments, however, only one of the two monomers includes an affinity element.

Adaptor Sequences

In any of the embodiments of the method described herein, the first transposon comprises a first adaptor sequence. In some embodiments, a secondary adaptor is added to a tagged fragment as described herein using a secondary adaptor carrier, which comprises a primer sequence and a secondary adaptor sequence. Adaptor sequences may comprise one or more functional sequences selected from the group consisting of universal sequences, primer sequences, index sequences, capture sequences, barcode sequences (used, e.g., for counting or error correction), cleavage sequences, sequencing-related sequences, and combinations thereof. In some embodiments, an adaptor sequence comprises a primer sequence. In other embodiments, an adaptor sequence comprises a primer sequence and an index or barcode sequence. A primer sequence may also be a universal sequence. This disclosure is not limited to the type of adaptor sequences which could be used and a skilled artisan will recognize additional sequences which may be of use for library preparation and next generation sequencing.

The adaptor sequences that are transferred to the 5' ends of a nucleic acid fragment by the tagmentation reaction (e.g., first adaptor sequence(s)) can comprise, for example, a universal sequence. A universal sequence is a region of nucleotide sequence that is common to two or more nucleic acid fragments. Optionally, the two or more nucleic acid fragments also have regions of sequence differences. A universal sequence that may be present in different members of a plurality of nucleic acid fragments can allow for the replication or amplification of multiple different sequences using a single universal primer that is complementary to the universal sequence.

In some embodiments, compositions and methods described herein employ two populations of transposome complexes. In some embodiments, each population comprises an adaptor sequence with a different primer sequence. In some embodiments, a first population comprises an A14 primer sequence and a second population comprises a B15 primer sequence.

Affinity Element and Affinity Binding Partner

An affinity element, as used herein, is a moiety that can be used to bind, covalently or no-covalently, to an affinity binding partner. In some aspects, the affinity element is on the transposome complex and the affinity binding partner is on the solid support.

In some embodiments, the affinity element can bind or is bound non-covalently to the affinity binding partner on the solid support, thereby non-covalently attaching the transposome complex to the solid support. In such embodiments, the affinity element comprises or is, for example, biotin, and the affinity binding partner comprises or is avidin or streptavidin. In other embodiments, the affinity element/binding partner combination comprises or is FITC/anti-FITC, digoxigenin/digoxigenin antibody, or hapten/antibody. Further suitable affinity pairs include, but not limited to, dithiobiotin-avidin, iminobiotin-avidin, biotin-avidin, dithiobiotin-succinilated avidin, iminobiotin-succinilated avidin, biotin-streptavidin, and biotin-succinilated avidin.

In some embodiments, the affinity element can bind to the affinity binding partner via a chemical reaction, or is bound covalently by reaction with the affinity binding partner on the solid support, thereby covalently attaching the transposome complex to the solid support. In some aspects, the affinity element/binding partner combination comprises or is amine/carboxylic acid (e.g., binding via standard peptide coupling reaction under conditions known to one of ordinary skill in the art, such as EDC or NHS-mediated coupling). The reaction of the two components joins the affinity element and binding partner through an amide bond. Alternatively, the affinity element and binding partner can be two click chemistry partners (e.g., azide/alkyne, which react to form a triazole linkage).

Cleavable Linkers

The ability to break bonds that link two molecular entities can be an effective tool to reduce capture of off target hybridization products, disrupting the possibility of generating genome wide off target captures during the first hybridization. As defined herein, a cleavable linker is a molecule with two functional heads joined together through a cleavable bond. The two functional heads serve to attach the linker to other moieties; in this case, the cleavable linker connects the 5' end of the first transposon sequence to an affinity element. An overview of cleavable linkers classified according to their cleavage conditions and biological applications are listed by Wagner et al., Bioorg. Med. Chem. 20, 571-582 (2012), which is incorporated herein by reference.

A cleavable linker as used herein is a linker that may be cleaved through chemical or physical means, such as, for example, photolysis, chemical cleavage, thermal cleavage, or enzymatic cleavage. In some embodiments the cleavage may be by biochemical, chemical, enzymatic, nucleophilic, reduction sensitive agent or other means.

In some embodiments, a cleavable linker can include a nucleotide or nucleotide sequence that may be fragmented by various means. For example, a cleavable linker may comprise a restriction endonuclease site; at least one ribonucleotide cleavable with an RNAse; nucleotide analogues cleavable in the presence of certain chemical agent(s); a diol linkage cleavable by treatment with periodate (for example); a disulfide group cleavable with a chemical reducing agent; a cleavable moiety that may be subject to photochemical cleavage; and a peptide cleavable by a peptidase enzyme or other suitable means. See e.g., U.S. Pat. Publ. Nos. 2012/0208705 and 2012/0208724, and PCT Publ. No. WO 2012/061832, each of which is incorporated by reference in its entirety.

Photo-cleavable (PC) linkers have been used in a variety of applications such as photocleavage-induced purification, protein engineering, photo-activation of compounds and biomolecules as well as photocleavable mass tagging for multiplex assays. PC linkers can contain a photolabile functional group that is cleavable by UV light of specific wavelength (300-350 nm). The PC linker may include, for example, a 10-atom unit that can be cleaved when exposed to UV light within the appropriate spectral range. Such photo-cleavable linkers and phosphoramidite reagents are commercially available from Integrated DNA technologies (IDT)), Ambergen, and Glen Research. Use of photo-cleavable nucleotide compositions is described in detail in U.S. Pat. Nos. 7,057,031, 7,547,530, 7, 897,737, 7,964,352 and 8,361,727, which are incorporated herein by reference in their entireties.

In some embodiments, cleavage is mediated enzymatically by incorporation of a cleavable nucleotide or nucleobase into the cleavable linker. Examples of such nucleobase or nucleotide moieties include, but are not limited to, uracil, uridine, 8-oxo-guanine, xanthine, hypoxanthine, 5,6-dihydrouracil, 5-methylcytosine, thymine-dimer, 7-methylguanosine, 8-oxo-deoxyguanosine, xanthosine, inosine, deoxyinosine, dihydrouridine, bromodeoxyuridine, uridine, 5-methylcytidine, deoxyuridine, 5,6-dihydroxythymine, thymine glycol, 5-hydroxy-5-methylhydanton, uracil glycol, 6-hydroxy-5,6-dihydrothymine, methyl tartronyl urea (1,2), or an abasic site.

In some embodiments, the cleavable linker includes a sufficient number of cleavable nucleotides to allow complete cleavage. In some embodiments, the linker includes 1 to 10 cleavable nucleotides. In some embodiments, the cleavable linker includes at least one cleavable nucleotide. In some embodiments, the linker includes at least 1, 2, 3, 4, 5, 6, 7, 8, 9, or 10 cleavable nucleotides. In a preferred embodiment, the cleavable linker comprises one or more uracil nucleotides and optionally other standard DNA bases. In some embodiments, an additional enzymatic step following PCR cleaves the cleavable linker at the cleavable nucleotide or nucleoside position. Examples of such enzymes include, but are not limited to, uracil DNA glycosylase (UDG, also referred to as uracil-N-glycosylase or UNG), formamidopyrimidine DNA glycosylase (Fpg), RNaseH, Endo III, Endo IV, Endo V, Endo VIII, Klenow, or apyrase. In some embodiments, a blend of enzymes comprising an enzyme that cleaves the uracil bases in nucleic acids and an AP nuclease is used. The effective concentration of the enzymes can range from 0.025 U/μl to 10 U/μl. In a preferred embodiment, the blend of enzymes is uracil DNA glycosylase and Endo IV. Commercial enzyme mixes for use in methods described herein include UDEM (Epicentre Biotechnologies). In yet another embodiment, the blend of enzymes is uracil DNA glycosylase and Endo VIII, commercially available as USER (New England Biolabs) or Uracil Cleavage System (Sigma Aldrich). Cleavage leaves the 5' affinity element (e.g., a biotin moiety) on a short oligonucleotide that could be removed by many methods known to a skilled artisan, for example, during nucleic acid purification such as the removal of target nucleic acids using a bead-based methodology that would leave small oligonucleotides uncaptured. The cleavage breaks the link between the affinity element (e.g., biotin) and the 5' tagged target fragment. In preferred embodiments, the cleavable linkers are adjacent and attached to the 5' end of the transposon end sequence of the transposon duplex. In some embodiments, the cleavable linker is linked to a biotin. In other embodiments, the biotin is affixed to a streptavidin coated bead.

Transposome Complexes and Transposons with 3' Linkers

In other aspects, a linker is connected to the 3' end of a second transposon, wherein the linker that is capable of connecting the second transposon to a solid support. Where the first and second transposons are part of a transposome complex, the linker serves to connect the complex to the solid support. In such aspects, a first end of the linker is attached to the 3' end of the second transposon and a second end of the linker is attached to an affinity element. The affinity element is capable of binding (covalently or non-covalently) to an affinity binding partner on a solid support. In some aspects, the affinity element is bound (covalently or non-covalently) to an affinity binding partner on the solid support, providing a solid support-bound transposome complex. In some aspects, the linker is a cleavable linker. These complexes are 3'-linker transposome complexes and support-bound 3'-linker transposome complexes. In some embodiments, the affinity element is a biotin and the affinity binding partner is streptavidin.

In one embodiment, the linker is covalently attached to the 3' end of the second transposon. In some embodiments, the linker is covalently attached to the 3' end of the second transposon end sequence. For example, the linker described herein may be covalently and directly attached the 3' end hydroxy group of the second transposon, thus forming a —O-linkage, or may be covalently attached through another group, such as a phosphate or an ester. Alternatively, the linker described herein may be covalently attached to a phosphate group of the second transposon or second transposon end sequence, for example, covalently attached to the 3' hydroxyl via a phosphate group, thus forming a —O—P(O)$_3$— linkage.

In some embodiments, the transposome complex described herein is immobilized to a solid support via the linker. In some such embodiments, affinity element is biotin and the solid support comprises streptavidin. In some further embodiment, the solid support comprises or is a bead. In one embodiment, the bead is a paramagnetic bead.

In some embodiments, the linker and affinity element have a structure of Formula (I):

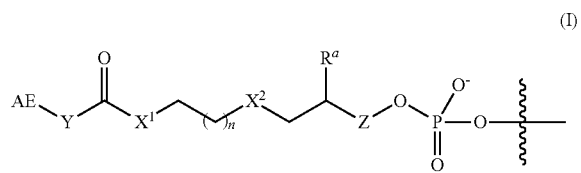

wherein:
AE is the affinity element;
Y is $C_{2-6}$alkylene;
$X^1$ is O, $NR^1$, or S;
wherein $R^1$ is H or $C_{1-10}$alkyl;
n is an integer from the group consisting of 1, 2, 3, 4, 5, and 6;
$X^2$ is O, $CH_2$, or S;
$R^a$ is H or —OH; and
Z is absent when $R^a$ is H, or is $CH_2$ when $R^a$ is H or OH;
wherein the ⁓ marks the connection point to the second transposon.

In some embodiments of Formula (I), AE is an optionally substituted biotin or an amino group. In other embodiments, AE is an optionally substituted biotin. In such embodiments, biotin is optionally substituted with $C_{1-4}$alkyl. In other embodiments, AE is biotin.

In some embodiments of Formula (I), Y is $C_{2-6}$alkylene. In other embodiments, Y is $C_{2-5}$alkylene. In other embodiments, Y is $C_{2-4}$alkylene. In other embodiments, Y is $C_{2-3}$alkylene. In other embodiments, Y is an unbranched alkylene. In other embodiments, Y is $C_2$alkylene. In other embodiments, Y is $C_3$alkylene. In other embodiments, Y is $C_4$alkylene. In other embodiments, Y is ethylene. In other embodiments, Y is propylene. In other embodiments, Y is butylene.

In some embodiments of Formula (I), $X^1$ is $NR^1$, wherein $R^1$ is H or $C_{1-10}$alkyl. In some such embodiments, $R^1$ is H. In some embodiments, $R^1$ is $C_{1-3}$alkyl. In other embodiments, $X^1$ is O. In other embodiments, $X^1$ is S.

In some embodiments of Formula (I), n is 1. In other embodiments, n is 2. In other embodiments, n is 3. In other embodiments, n is 4.

In some embodiments of Formula (I), $X^2$ is $CH_2$. In some other embodiments, $X^2$ is O. In other embodiments, $X^2$ is S.

In some embodiments of Formula (I), $R^a$ is H. In other embodiments, $R^a$ is —OH.

In some embodiments of Formula (I), Z is absent and $R^a$ is H. In some embodiments, Z is $CH_2$ and $R^a$ is H. In some embodiments, Z is $CH_2$ and $R^a$ is OH.

In some embodiments, the linker and affinity element have the structure of Formula (I'):

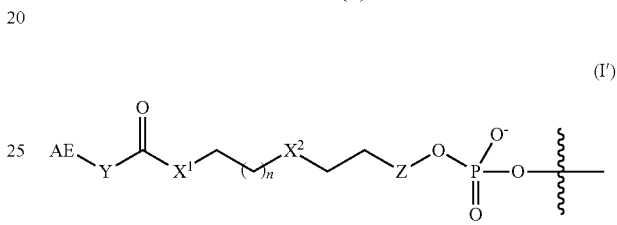

wherein AE, Y, $X^1$, n, $X^2$, are defined as described herein for Formula (I), and Z is absent or is $CH_2$.

In some embodiments, the linker and affinity element have the structure of Formula (Ia):

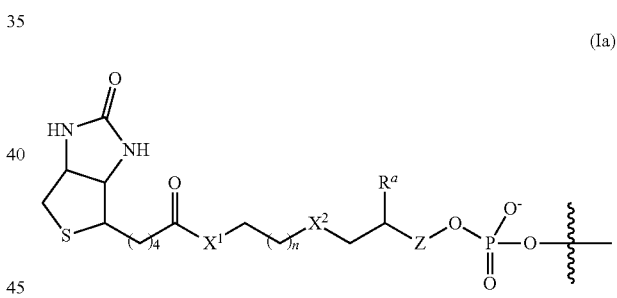

wherein $X^1$, n, $X^2$, $R^a$, and Z are defined as described herein for Formula (I). In some embodiments, $R^a$ is H.

In some embodiments, the linker and affinity element have the structure of Formula (Ib):

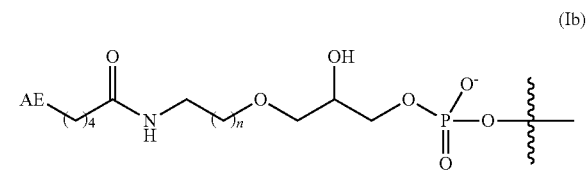

wherein AE is as defined for Formula (I) herein; and n is 1 or 2.

In some aspects of Formula (Ib), AE is optionally substituted biotin or an amino group. In some embodiments, AE is biotin.

In some embodiments, the linker and affinity element have the structure of Formula (Ic):

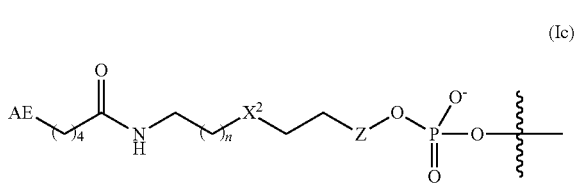

(Ic)

where AE is as defined for Formula (I) herein; $X^2$ is O or $CH_2$, n is 1 or 2; and Z is absent or is $CH_2$.

In some embodiments of Formula (Ic), AE is optionally substituted biotin or an amino group. In some embodiments, AE is biotin. In some embodiments, $X^2$ is O. In some embodiments, $X^2$ is $CH_2$. In some embodiments, n is 1. In some embodiments, n is 2. In some embodiments, Z is absent. In some embodiments, Z is $CH_2$. In some embodiments, n is 1, $X^2$ is O, and Z is absent. In some embodiments, n is 1, $X^2$ is $CH_2$, and Z is $CH_2$.

In some embodiments, the linker and affinity element have a structure selected from the group consisting of:

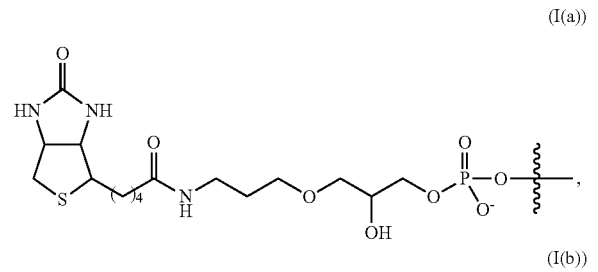

(I(a))

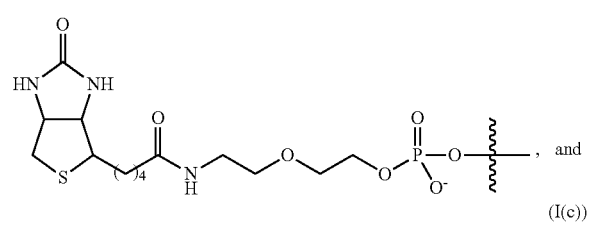

(I(b)), and

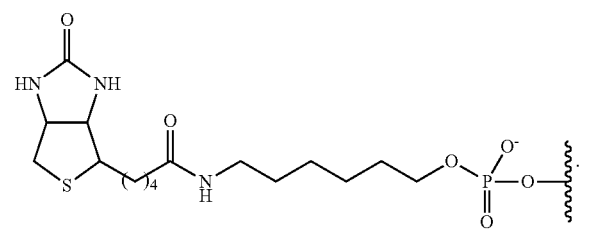

(I(c))

In some embodiments, the linker and affinity element have the structure (I(c)).

In some embodiments, the adaptor sequence comprises a primer sequence. In some embodiments, the primer sequence is an A14 or a B15 primer sequence. In some embodiments, the primer sequence is a P5 primer sequence or a P7 primer sequence. In some embodiments, the transposase is a dimer, each monomer is bound to a transposon duplex with an adaptor sequence as described herein, where the adaptor sequence in each monomer is the same. In embodiments where the transposase is a dimer, one or both monomers includes the linker connecting the transposome complex to the solid support. Each monomer includes a first transposon with an adaptor sequence.

Solid Support

The terms "solid surface," "solid support," and other grammatical equivalents refer to any material that is appropriate for or can be modified to be appropriate for the attachment of the transposome complexes. As will be appreciated by those in the art, the number of possible substrates is multitude. Possible substrates include, but are not limited to, glass and modified or functionalized glass, plastics (including acrylics, polystyrene and copolymers of styrene and other materials, polypropylene, polyethylene, polybutylene, polyurethanes, TEFLON, etc.), polysaccharides, nylon or nitrocellulose, ceramics, resins, silica or silica-based materials including silicon and modified silicon, carbon, metals, inorganic glasses, plastics, optical fiber bundles, beads, paramagnetic beads, and a variety of other polymers.

In some such embodiments, the transposome complex is immobilized on the solid support via the linker as described herein. In some further embodiments, the solid support comprises or is a tube, a well of a plate, a slide, a bead, or a flowcell, or a combination thereof. In some further embodiment, the solid support comprises or is a bead. In one embodiment, the bead is a paramagnetic bead.

In the methods and compositions presented herein, transposome complexes are immobilized to a solid support. In one embodiment, the solid support is a bead. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and TEFLON, as well as any other materials outlined herein for solid supports. In certain embodiments, the microspheres are magnetic microspheres or beads, for example paramagnetic particles, spheres or beads. The beads need not be spherical; irregular particles may be used. Alternatively or additionally, the beads may be porous. The bead sizes range from nanometers, e.g., 100 nm, to millimeters, e.g., 1 mm, with beads from about 0.2 micron to about 200 microns being preferred, and from about 0.5 to about 5 micron being particularly preferred, although in some embodiments smaller or larger beads may be used. The bead may be coated with an affinity binding partner, for example the bead may be streptavidin coated. In some embodiments the beads are streptavidin coated paramagnetic beads, for example, Dynabeads MyOne streptavidin $C_1$ beads (Thermo Scientific catalog #65601), Streptavidin MagneSphere Paramagnetic particles (Promega catalog #Z5481), Streptavidin Magnetic beads (NEB catalog #S1420S) and MaxBead Streptavidin (Abnova catalog #U0087). The solid support could also be a slide, for example a flowcell or other slide that has been modified such that the transposome complex can be immobilized thereon.

In some embodiments, the affinity binding partner is present on the solid support or bead at a density of from 1000 to about 6000 pmol/mg, or about 2000 to about 5000 pmol/mg, or about 3000 to about 5000 pmol/mg, or about 3500 to about 4500 pmol/mg.

In one embodiment, the solid surface is the inner surface of a sample tube. In one example, the sample tube is a PCR tube. In another embodiment, the solid surface is a capture membrane. In one example, the capture membrane is a biotin-capture membrane (for example, available from Promega Corporation). In another example, the capture membrane is filter paper. In some embodiments of the present disclosure, solid supports comprised of an inert substrate or matrix (e.g. glass slides, polymer beads etc.) which has been functionalized, for example by application of a layer or coating of an intermediate material comprising reactive groups which permit covalent attachment to molecules, such as polynucleotides. Examples of such supports include, but are not limited to, polyacrylamide hydrogels supported on an inert substrate such as glass, particularly polyacrylamide hydrogels as described in WO2005/065814 and US2008/0280773, the contents of which are incorporated herein in their entirety by reference. The methods of tagmenting (fragmenting and tagging) DNA on a solid surface for the construction of a tagmented DNA library are described in WO2016/189331 and US2014/0093916A1, which are incorporated herein by reference in their entireties.

Some further embodiments of the present disclosure relate to a solid support comprising a transposome complex immobilized thereon as described herein, where the linker and affinity element have a structure of Formula (I), (I'), (Ia), (Ib), (Ic), (I(a)), (I(b)), or (I(c)) as described herein. In some embodiments, the transposome complex described herein is immobilized to a solid support via the affinity element. In some such embodiments, the solid support comprises streptavidin as the affinity binding partner and the affinity element is biotin. In some further embodiment, the solid support comprises or is a bead. In one embodiment, the bead is a paramagnetic bead.

In some embodiments, transposome complexes are immobilized on a solid support, such as a bead, at a particular density or density range. The density of complexes on beads, as that term is used herein, refers to the concentration of transposome complexes in solution during the immobilization reaction. The complex density assumes that the immobilization reaction is quantitative. Once the complexes are formed at a particular density, that density remains constant for the batch of surface-bound transposome complexes. The resulting beads can be diluted, and the resulting concentration of complexes in the diluted solution is the prepared density for the beads divided by the dilution factor. Diluted bead stocks retain the complex density from their preparation, but the complexes are present at a lower concentration in the diluted solution. The dilution step does not change the density of complexes on the beads, and therefore affects library yield but not insert (fragment) size. In some embodiments, the density is between about 5 nM and about 1000 nM, or between about 5 and 150 nM, or between about 10 nM and 800 nM. In other embodiments, the density is about 10 nM, or about 25 nM, or about 50 nM, or about 100 nM, or about 200 nM, or about 300 nM, or about 400 nM, or about 500 nM, or about 600 nM, or about 700 nM, or about 800 nM, or about 900 nM, or about 1000 nM. In some embodiments, the density is about 100 nM. In some embodiments, the density is about 300 nM. In some embodiments, the density is about 600 nM. In some embodiments, the density is about 800 nM. In some embodiments, the density is about 100 nM. In some embodiments, the density is about 1000 nM.

In some embodiments, the solid support is a bead or a paramagnetic bead, and there are greater than 10,000, 20,000, 30,000, 40,000, 50,000, or 60,000 transposome complexes bound to each bead.

Figure 7A:
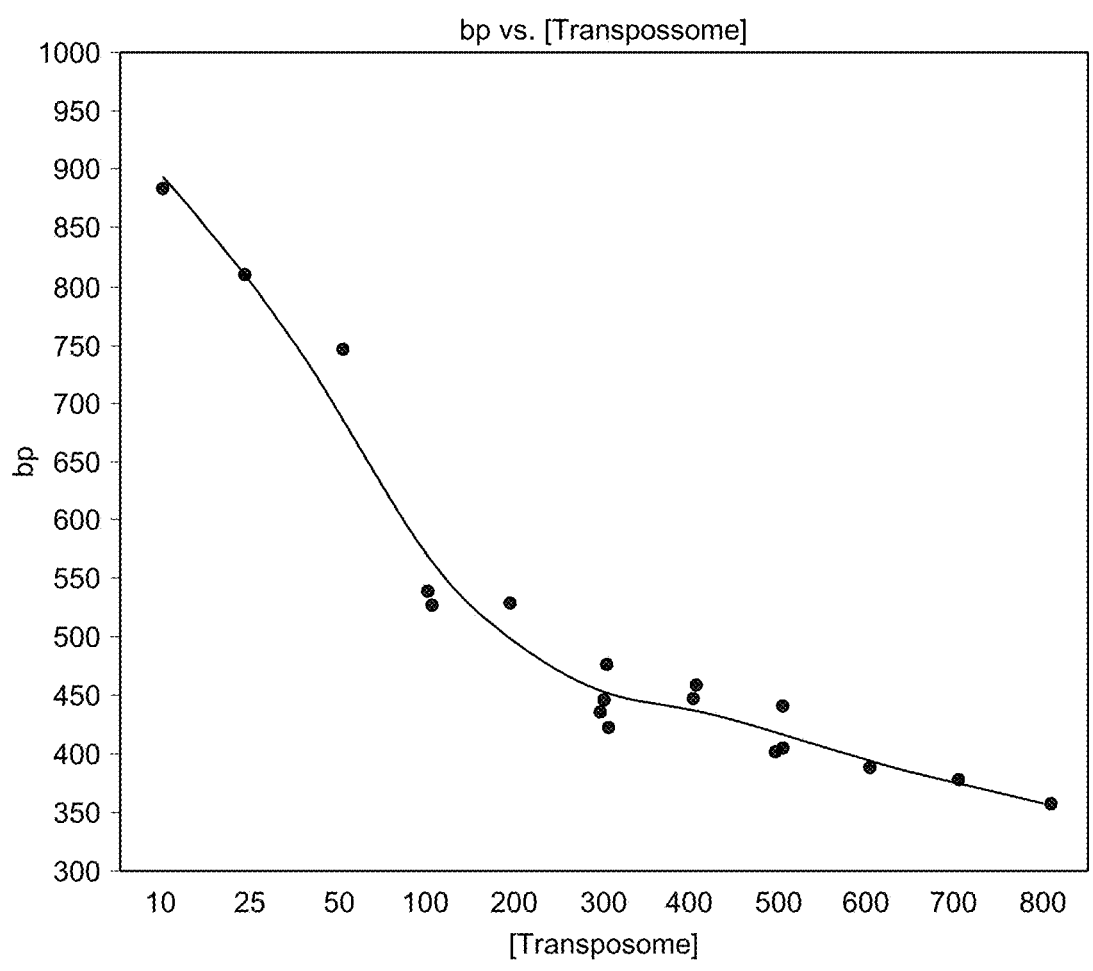
FIG. 7A demonstrates the target insert size of DNA molecules as a function of the complex density using the streptavidin bead-based solid-phase library preparation where the beads comprise immobilized transposome complex bounded thereto through 3'-biotinylated linker.
Figure 7B:
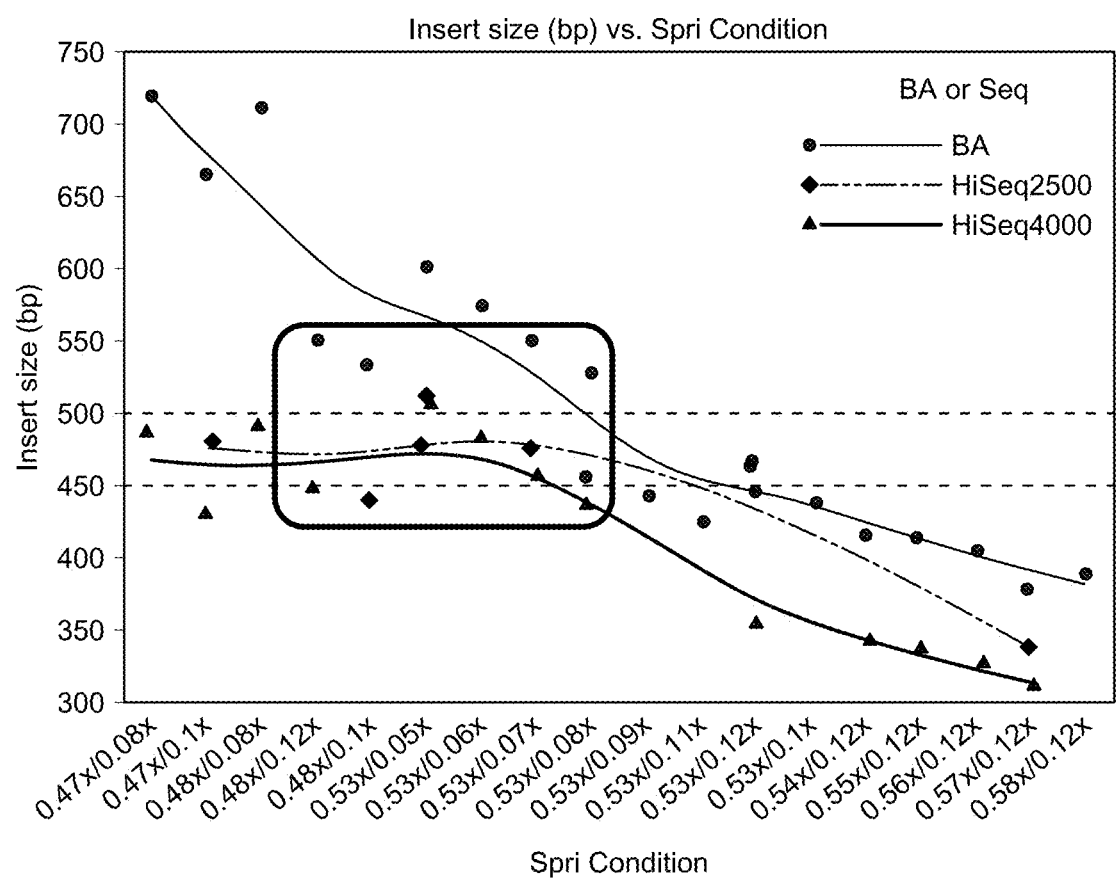
FIG. 7B is a line chart showing the target insert size of the DNA molecules as a function of SPRI condition using streptavidin beads with immobilized transposome complex comprising a hyperactive Tn5 transposase and a 3'-biotinylated linker, and a complex density of 100 nM.
Figure 7C:
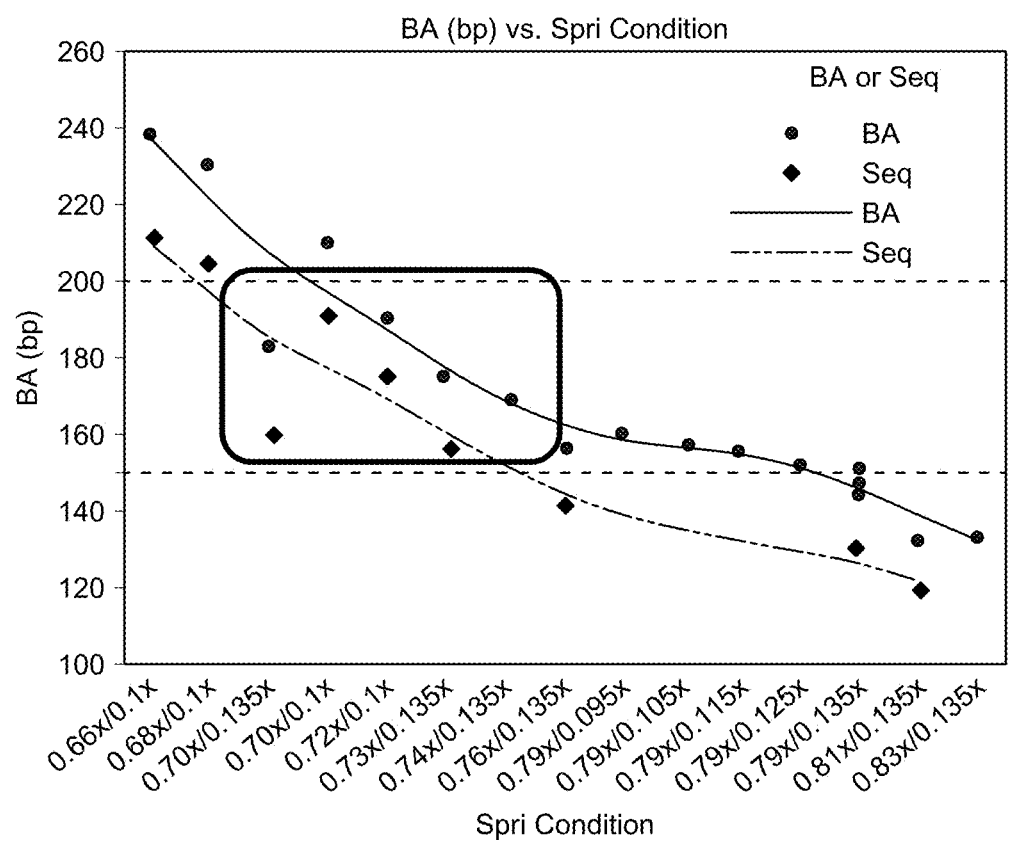
FIG. 7C is a line chart showing the target insert size of the DNA molecules as a function of SPRI condition using streptavidin beads with immobilized transposome complex comprising a hyperactive Tn5 transposase and a 3'-biotinylated linker, and a complex density of 600 nM.

Different densities of solid support-bound transposome complexes yield fragments of different lengths (e.g., different insert sizes). For example, as shown in FIGS. 7A, 7B, and 7C, varying complex density leads to varying insert sizes. Insert sizes may be from about 50 bp to about 1000 bp, or about 100 to about 600 bp, or about 175 to about 200 bp, or about 500 bp.

Methods of Preparing Modified Oligonucleotides and Immobilized Transposome Complexes The disclosure further provides for methods of preparing modified oligonucleotides, transposome complexes, and solid support-bound transposome complexes as described herein. In some aspects, such methods comprise treating a transposase with the first and second transposons as described herein under conditions suitable for forming the complex. Methods for preparing a solid support-bound transposome complex comprise incubating a transposome complex as described herein with a solid support comprising an affinity binding partner under conditions sufficient for the affinity element to bind (covalently or non-covalently) with the affinity binding partner.

In some embodiments are method of preparing modified oligonucleotides. In some aspects, methods of preparing modified oligonucleotides with a linker connected to an affinity element are known in the art. Certain methods contemplated herein comprise reacting a linker (or cleavable linker) reagent comprising a first reactive functional group (L-FG1) with a nucleotide comprising a second reactive functional group (N-FG2), where by the first and second reactive functional groups react to form a Linker-Nucleotide product with a covalent bond (CB) between the linker and the nucleotide (L-(CB)-N). In some embodiments, the linker reagent includes the AE moiety (AE-Linker-FG1). In other embodiments, the linker reagent comprises a portion of the linker structure, and the AE is installed through a second coupling reaction to generate the full AE-Linker structure.

The first reactive functional group may be, for example, carboxyl, activated carboxyl (such as an ester, NHS ester, acyl halide, anhydride, or the like), azido, alkyne, formyl, or amino. In some embodiments, the first reactive functional group is an activated carboxyl, preferably an NHS ester.

The second reactive functional group may be at any suitable position on the nucleotide. In some embodiments, the second reactive functional group is at the 3' hydroxyl position or the 5' phosphate position of the nucleotide, either in place of the natural substituent or appended thereto via a tether, such as an alkylene or heteroalkylene group, or a phosphate group in the case of a nucleotide hydroxyl. In some embodiments, the second reactive functional group comprises a $C_{2-10}$-alkylamino group. In some embodiments, the second reactive functional group comprises a hexylamino group. In some embodiments, the second reactive functional group is $-OP(O)_3-(CH_2)_6-NH_2$. In some embodiments, the second reactive functional group is connected to the nucleotide through the 3' hydroxyl of the nucleotide via a phosphate tether.

The modified nucleotide may be part of an oligonucleotide prior to attaching the linker, in which case the nucleotide may be, for example, at the 3' end or the 5' end of the oligonucleotide. Alternatively, the linker is attached to the nucleotide first, and the modified nucleotide is used as the starting material in synthesizing an oligonucleotide by standard means.

In some embodiments, the linker of Formula (I) is connected to the 3' position of a nucleotide, such as a cytidine. In some embodiments, the method of making the modified nucleotide comprises reacting a compound of Formula (II) with a compound of Formula (III):

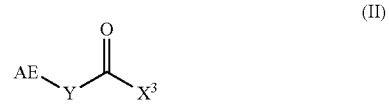

(II)

-continued

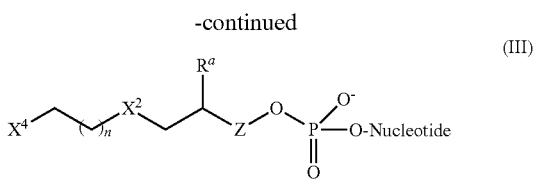
(III)

wherein AE, Y, n, $X^2$, $R^a$, and Z are as defined herein;
—C(O)$X^3$ is an activated ester, such as an ester, acyl halide, ester anhydride, or NHS ester; and
$X^4$ is an —OH or —NH$_2$ group;
to form a compound of [Formula (I)]-Nucleotide.

In some embodiments, the compound of Formula (II) is AE-(CH$_2$)$_4$C(O)—O—NHS and the compound of Formula (III) is H$_2$N—(CH$_2$)$_6$—OP(O)(O$^-$)O-Nucleotide, and the product is AE-(CH$_2$)$_4$C(O)—NH—(CH$_2$)$_6$—OP(O)(O$^-$)O-Nucleotide. In some embodiments, the phosphate is connected at the 3' hydroxyl group of a nucleotide, such as a cytidine. In some embodiments, the compound of [Formula (I)]-Nucleotide (or AE-(CH$_2$)$_4$C(O)—NH—(CH$_2$)$_6$—OP(O)(O$^-$)O-Nucleotide) is reacted with additional nucleotides to form [Formula (I)]-Oligonucleotide (or AE-(CH$_2$)$_4$C(O)—NH—(CH$_2$)$_6$—OP(O)(O$^-$)O-Oligonucleotide). In some embodiments, the second transposon is [Formula (I)]-Oligonucleotide (or AE-(CH$_2$)$_4$C(O)—NH—(CH$_2$)$_6$—OP(O)(O$^-$)O-Oligonucleotide).

The present disclosure also relates to methods of preparing transposome complexes using the modified oligonucleotides described herein. Such methods comprise mixing a transposase, a first transposon, and a second transposon, as defined herein, where the first and second transposon end sequences are annealed to one another, to form the transposome complex. As described herein, one of the first and second transposons comprises an affinity element (at the 5' end in the case of the first transposon; at the 3' end in the case of the second transposon). In some embodiments, the method further comprises binding the affinity element to a solid support comprising an affinity binding partner. The binding may be performed before or after the formation of the transposome complex.

Preparing Sequencing Fragments—Amplification of Tagged Fragments

In some aspects are provided methods for preparing sequencing fragments from a target nucleic acid, the method comprising providing a solid support comprising a transposome complex described herein immobilized thereon as described herein; contacting the solid support with a target nucleic acid under conditions to fragment the target nucleic acid and ligate a first transposon to the 5' end of the fragments, whereby the fragment becomes immobilized on the solid support. In some aspects, the method further comprises amplifying the fragmented nucleic acids. In some embodiment, the fragment condition is a condition suitable for tagmentation by using the transposome complex to fragment and tag the target nucleic acid.

In some embodiments of the methods described herein, following the fragmenting and tagging, the methods further comprise removing the transposase from the 5' tagged target fragments to provide non-complexed 5' tagged target fragments. Removal of the transposase may be accomplished under chemical conditions, such as, treatment with a denaturing agent such as sodium dodecyl sulfate (SDS). Such methods may further comprise generating fully duplexed versions of the 5' tagged target fragments. Generating the full duplex may comprise removing the annealed (but not ligated) second transposon (AE-linker-second transposon) from the 5' tagged target fragments and extending the 5' tagged target fragments to generate fully duplexed 5' tagged target fragments. The generating may be accomplished, for example, by heating the non-complexed 5' tagged target fragments to a temperature sufficient to selectively denature the second transposon, leaving the remaining duplex region of the fragment intact. Extending may be accomplished in the presence of dNTP and a suitable polymerase. Alternatively, the generating may be accomplished in one reaction, by incubating the non-complexed 5' tagged target fragments in the presence of single nucleotides (dNTPs) and a polymerase. In some embodiments, the incubating includes heating at one or more temperatures sufficient to denature the annealed second transposon and extend the remaining duplexes. In other embodiments, the polymerase is a strand-displacing polymerase, which serves to remove the second transposon and extend the remaining duplex to generate fully duplexed 5' tagged target fragments. Suitable polymerases include KAPA HiFi, Pfu, and similar enzymes. Suitable polymerases include strand-displacing polymerases such as Bst, Bsu Vent, Klenow, and similar enzymes.

In some aspects, the methods further comprise amplifying the fully duplexed 5' tagged target fragments. The amplifying may be done by any suitable amplification method, such as polymerase chain reaction (PCR), rolling circle amplification (RCA), or multiple displacement amplification (MDA). In some embodiments, amplifying is done by PCR. In some embodiments, the amplification and extending are done in one reaction step, by reacting with dNTPs in the presence of a polymerase.

In some embodiments, the amplifying serves to add one or more secondary adaptor sequences to the fully duplexed 5' tagged target fragments to form sequencing fragments. The amplifying is accomplished by incubating a fully duplexed 5' tagged target fragment comprising a primer sequence at each end with a secondary adaptor carrier, single nucleotides, and a polymerase under conditions sufficient to amplify the target fragments and incorporate the secondary adaptor carrier (or complement thereof), wherein the secondary adaptor carrier comprises the complement to the primer sequence and a secondary adaptor sequence.

In some embodiments, the secondary adaptor carrier comprises a primer sequence, an index sequence, a barcode sequence, a purification tag, or a combination thereof. In some embodiments, the secondary adaptor carrier comprises a primer sequence. In some embodiments, the secondary adaptor carrier comprises an index sequence. In some embodiments, the secondary adaptor carrier comprises an index sequence and a primer sequence.

In some embodiments, the fully duplexed 5' tagged target fragments comprise a different primer sequence at each end. In such embodiments, each secondary adaptor carrier comprises the complement to one of the two primer sequences. In some embodiments, a two primer sequences are an A 14 primer sequence and a B15 primer sequence.

In some embodiments, a plurality of secondary adaptors are added by amplification. In some embodiments, the secondary adaptor carriers each comprise one of two primer sequences. In some embodiments, the secondary adaptor carriers each comprise one of a plurality of index sequences. In some embodiments, the secondary adaptor carriers comprise secondary adaptors with a P5 primer sequence and secondary adaptors with a P7 primer sequence.

In some embodiments, the sequencing fragments are deposited on a flow cell. In some embodiments, the sequencing fragments are hybridized to complementary primers grafted to the flow cell or surface. In some embodiments, the sequences of the sequencing fragments are detected by array sequencing or next-generation sequencing methods, such as sequencing-by-synthesis.

The P5 and P7 primers are used on the surface of commercial flow cells sold by Illumina, Inc., for sequencing on various Illumina platforms. The primer sequences are described in U.S. Patent Publication No. 2011/0059865 A1, which is incorporated herein by reference in its entirety. Examples of P5 and P7 primers, which may be alkyne terminated at the 5' end, include the following:

```
                                    (SEQ ID NO. 1)
P5: AATGATACGGCGACCACCGAGAUCTACAC (SEQ ID NO. 2)
P7: CAAGCAGAAGACGGCATACGAG*AT
``` and derivatives thereof. In some examples, the P7 sequence includes a modified guanine at the G* position, e.g., an 8-oxo-guanine. In other examples, the * indicates that the bond between the G* and the adjacent 3' A is a phosphorothioate bond. In some examples, the P5 and/or P7 primers include unnatural linkers. Optionally, one or both of the P5 and P7 primers can include a poly T tail. The poly T tail is generally located at the 5' end of the sequence shown above, e.g., between the 5' base and a terminal alkyne unit, but in some cases can be located at the 3' end. The poly T sequence can include any number of T nucleotides, for example, from 2 to 20. While the P5 and P7 primers are given as examples, it is to be understood that any suitable amplification primers can be used in the examples presented herein.

In some embodiments, the amplifying step of the method comprises PCR or isothermal amplification. In some embodiments, the amplifying step of the method comprises PCR.

DESCRIPTION OF DRAWINGS

FIG. 1 illustrates the exemplary steps of a method of preparing transposome complexes and affixing them to a solid surface (such as a bead) through an affinity element linked to the 5' end of the first transposon. In this example, two populations (130a and 130b) of annealed first and second transposons (oligonucleotides comprising an annealed double stranded region comprising transposon end sequence and a single stranded region), where in each population the first transposon includes one of two adaptor sequences and an affinity element (110, where * indicates affinity element), such as biotin, at the 5' end. For example, a plurality of biotinylated first and second transposons comprising the two adaptor sequences (e.g., primer sequences such as A14 and B15) are generated. As depicted, the strand of the duplex transposon sequence that will be transferred into the template nucleic acids is the first transposon, which has the affinity element (e.g., biotin). In step 115, each population of oligonucleotides (130a and 130b) is complexed with transposase monomers such as Tn5 (135), typically in separate reactions, to create two discrete populations of transposome complexes (140), each with a different adaptor sequence (e.g., primer sequences such as A14 and B15). After the two populations of complexes are formed, they are immobilized on a substrate, beads in this example (120). In some embodiments, the two populations are combined before immobilization, yielding a solid surface or bead comprising complexes from each population. In other embodiments, the two populations are immobilized separately, yielding two solid surfaces or beads each comprising one of the two complex types. Following transposome complex formation, the transposomes 140 are bound to the surface 145 coated with an affinity binding partner, such as streptavidin.

Figure 2:
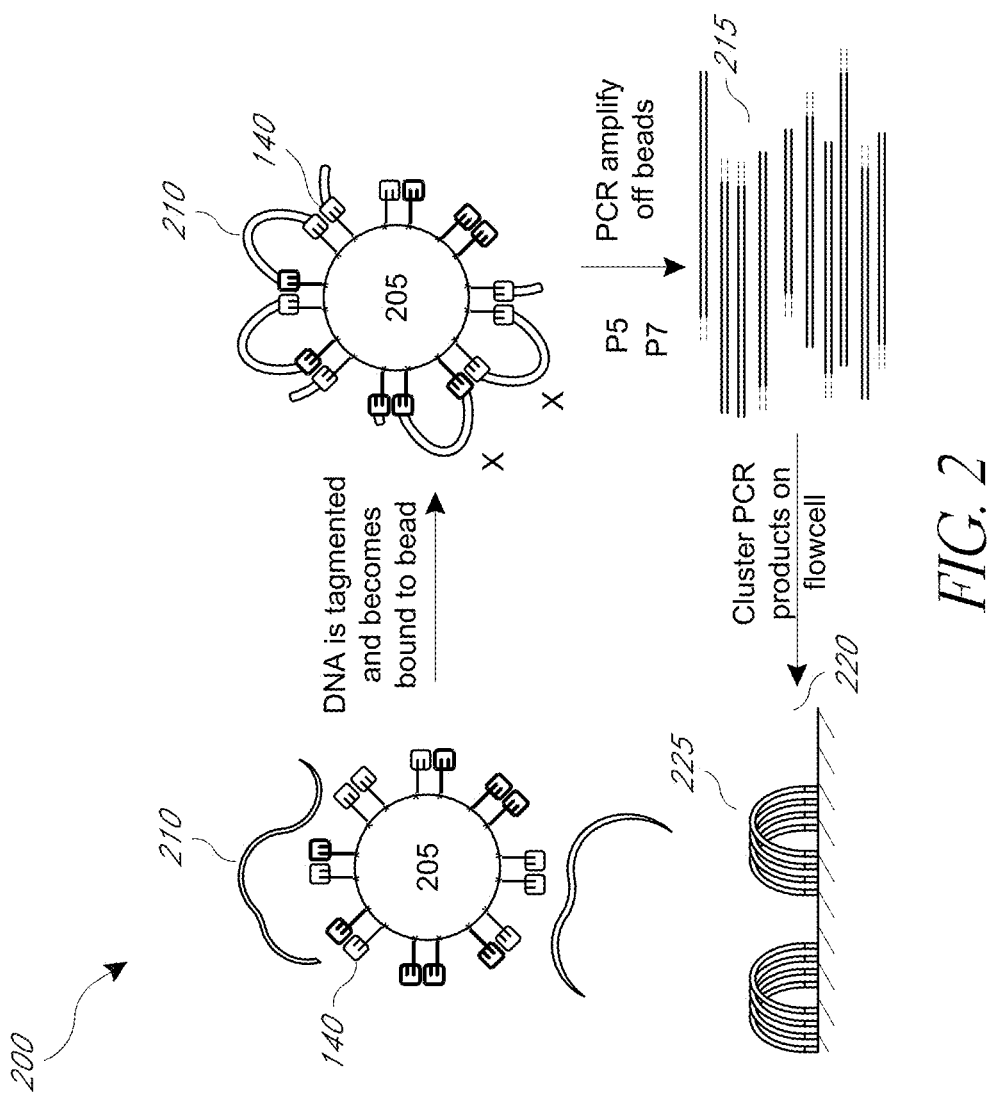
FIG. 2 illustrates a schematic diagram of an exemplary tagmentation process on a bead surface through cluster formation on a flowcell.

FIG. 2 exemplifies a tagmentation and library preparation process 200 on a bead surface following immobilization of the transposome using a 5' linker strategy described herein. Shown in process 200 is bead 205 with transposomes 140 bound thereon. DNA 210 is added to a sample of beads. As DNA 210 contacts transposomes 140, the DNA is tagmented (fragmented and tagged) and is bound to beads 205 via transposomes 140. Bound and tagmented DNA may be PCR amplified to generate a pool of bead-free amplicons 215. The PCR step may be used to incorporate secondary adaptor sequences, such as primer sequences (e.g., P5 and P7). Amplicons 215 may be transferred to the surface of a flow cell 220, for example, by grafting to or hybridizing to complementary primers on the flow cell surface. A cluster generation protocol (e.g., a bridge amplification protocol or any other amplification protocol that may be used for cluster generation) may be used to generate a plurality of clusters 225 on the surface of a flow cell. Clusters are clonal amplification products of tagmented DNA. Clusters are now ready for the next step in a sequencing protocol. An example of the tagmentation process on a bead surface is described in detail in PCT Publ. No. WO2016/189331, which is incorporated by reference in its entirety.

FIG. 3 illustrates issues that can arise when using 5' linked transposome complexes. Step 300 pictorially illustrates the tagmentation process of transposome complexes 140 immobilized on bead 305 with genomic DNA 315, followed by subsequent amplification and target enrichment including the capture of non-target nucleic acids. An immobilized library of tagmented genomic DNA is depicted in 310. The streptavidin-coated capture beads that have tagmented DNA thereon can be washed (320), using a wash buffer comprising, for example 5% SDS, 100 mM Tris-HCl pH7.5. 100 mM NaCl, and 0.1% Tween 20, thereby denaturing the transposase from the transposome complex. The supernatant can then be removed following the wash step, via magnetic capture of the streptavidin coated paramagnetic particles (e.g., beads) and the capture beads comprising the immobilized tagmented libraries can be retained, and further washed using 100 mM Tris-HCl pH7.5. 100 mM NaCl, 0.1% Tween 20. The bound oligonucleotides are extended at 330 to form bound duplexes with full complementarity.

At 340, target amplification proceeds via thermal cycling to amplify the tagmented DNA by methods known to a skilled artisan. For example, a solution of PCR reagents (e.g., a mixture comprising minimally a PCR buffer, deoxynucleotides, a divalent cation, and a DNA polymerase) and additives required for efficient amplification can be added to the bead-containing solution and the tagmented DNA bound to the capture bead can be amplified by thermal cycling (e.g., 10 thermal cycles), a methodology known to a skilled artisan. At 350, the amplified tagmented DNA can be optionally purified using, for example, a purification column (e.g., a Zymo spin column) and eluted. The amplified tagmented DNA can also be optionally purified using SPRI or Ampure XP beads (Beckman Coulter), the method of purification is not limiting to the present disclosure.

At step 360, the tagmented libraries can be enriched using a protocol as described in NEXTERA Rapid Capture enrichment protocol (Illumina) or any other target capture method. The biotinylated genomic fragments from the beginning of the library prep are present in the post-amplification mixture (370) and could compete with biotinylated target probes (380), serving as whole genome hybridization probes during target enrichment. The presence of these biotinylated genomic fragments at this stage could compromise the efficiency of the enrichment. Additionally, biotinylated genomic fragments could be generated during PCR amplification by polymerase priming and extension of free biotinylated adaptors that were not consumed in the tagmentation reaction, thereby adding additional off-target capture probes to the target enrichment step.

The present disclosure provides several solutions to this problem. In one approach described herein, one or more cleavable linkers is included between the affinity element and the adaptor sequence of the first transposon. Once tagmentation is completed and the tagmented nucleic acid is amplified the cleavable linker could be cleaved, releasing the biotinylated portion and minimizing or eliminating off target capture. This modification drastically and surprisingly decreases off-target capture and improves enrichment relative to other bead-based tagmentation methodologies. Second, the affinity element is moved over to the 3' end of the second transposon, and is attached through an optionally cleavable linker.

Figure 4:
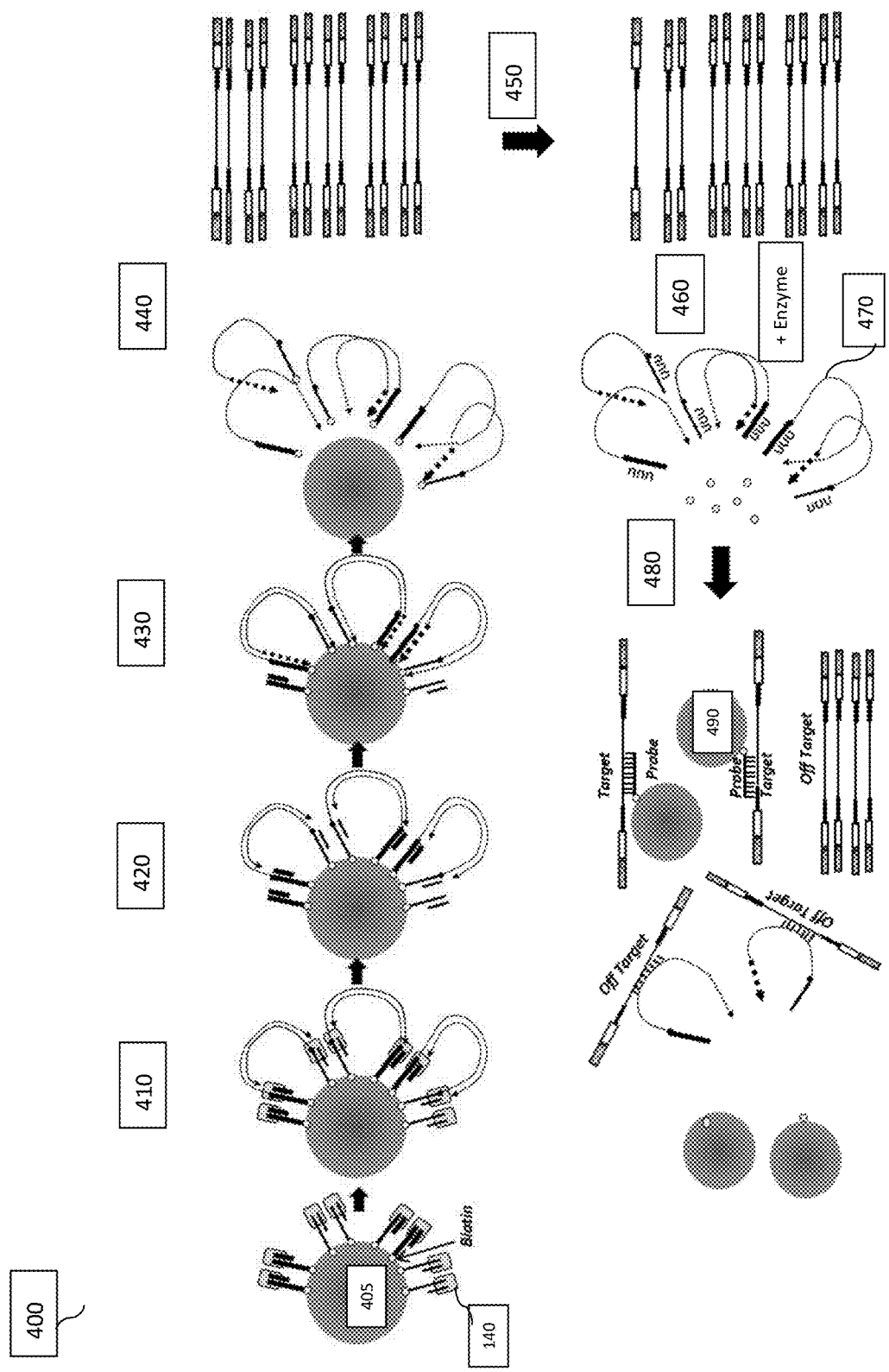
FIG. 4 shows exemplary steps of the method of fragmenting and tagging DNA using transposome complexes immobilized on a bead surface using an enzymatically cleavable linker followed by target enrichment.

FIG. 4 pictorially illustrates the steps of a method 400 of fragmenting and tagging DNA using transposome complexes immobilized on a solid surface using a cleavable linker. Referring to FIG. 4, steps 410, 420, 430, 440, and 450 are as described for FIGS. 3 (310, 320, 330, 340, and 350, respectively) with the exception that the biotinylated genomic fragments present in the post-amplification mixture (470) contain a cleavable linker (e.g., a linker comprising one or more uracils). In step 460, the biotin is cleaved off of the genomic fragments by cleaving the linker using the appropriate cleavage agent. For the uracil example, cleavage would be accomplished with a uracil cleavage enzyme (e.g., Uracil DNA Excision Mix from Epicentre, for example). During the enrichment step 480, the off-target genomic fragments are no longer biotinylated and therefore are not captured like the biotinylated target probes (490). In this way, the method decreases off-target capture and increases the efficiency of the target enrichment when compared to the 5' linked approach without a cleavable linker.

Figure 5A:
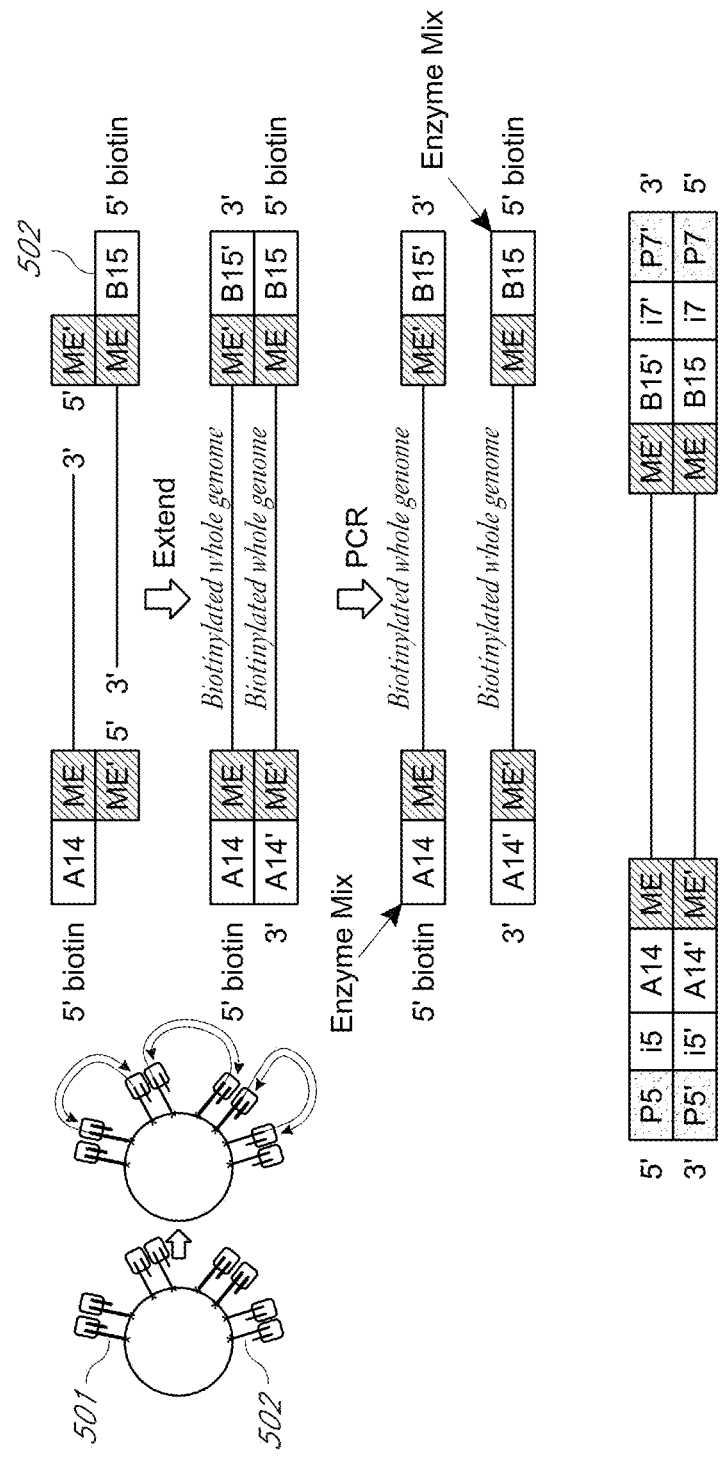
FIG. 5A shows an example of a biotinylated 5' end of a transposon sequence attached to a solid surface for tagmentation and subsequent amplification.

A bead-based tagmentation approach using adaptor sequences that include an affinity element such as biotin at the 5' end is shown in FIG. 5A. Briefly, the affinity element at the 5' end of two types of adaptor oligonucleotides 501 and 502 is used to attach the two populations of transposomes to a surface (e.g., one with an A14 adaptor sequence and one with a B15 adaptor sequence). ME and ME' are the transposon end sequences. The tagmentation event creates 5' tagged fragments from a target nucleic acid, such as genomic DNA. Some of the fragments include an A14 at the 5' end of one strand and a B15 at the 5' end of the other strand of the fragment as shown. Fragments are extended and/or reacted by amplification, such as PCR, optionally in the presence of secondary adaptor carriers, to prepare full duplexes or amplicons, optionally comprising secondary adaptors (e.g., primer sequences such as P5 and P7 and/or index sequences as shown in the bottom image). When biotin/streptavidin are used, affinity bonds are broken during PCR, leaving biotinylated fragment amplicons in solution, which can complicate subsequent enrichment efforts. Alternatively, in FIG. 5B, the attachment of affinity element and linker is changed to a 3' position on the second transposon. In this case, the affinity element and linker are attached to the 3' end of the complementary transposon end sequence 503 (ME' sequence). In this configuration, the first transposons 501 and 502 do not include an affinity element. With this process, the tagmentation event creates non-labeled fragmented genomic DNA, as the first transposon (which lacks an affinity element) is transferred to the fragment, and the affinity element is connected merely due to hybridization of the second transposon to the first transposon. The adaptor sequences A14-ME, ME, B15-ME, ME', A14, B15, and ME are provided below:

```
                                          (SEQ ID NO: 3)
A14-ME:  5'-TCGTCGGCAGCGTCAGATGTGTATAAGAGACAG-3'

(SEQ ID NO: 4)
B15-ME:  5'-GTCTCGTGGGCTCGGAGATGTGTATAAGAGACAG-3'

(SEQ ID NO: 5)
ME':     5'-phos-CTGTCTCTTATACACATCT-3'

(SEQ ID NO: 6)
A14:     5'-TCGTCGGCAGCGTC-3'

(SEQ ID NO: 7)
B15:     5'-GTCTCGTGGGCTCGG-3'

(SEQ ID NO.: 8)
ME:      AGATGTGTATAAGAGACAG
```

Target Nucleic Acid

The target nucleic acid can be any type that comprises DNA, RNA, cDNA, or the like. For example, the target nucleic acid may be in a variety of states of purification, including purified nucleic acid. However, the nucleic acid need not be completely purified or purified at all, and can be part of a biological sample, for example, a raw sample lysate, a bodily fluid, blood, plasma, or serum, or may be otherwise mixed with protein, other nucleic acid species, other cellular components, and/or any other contaminants. In some embodiments, the biological sample comprises a mixture of nucleic acids (such as DNA), protein, other nucleic acid species, other cellular components, and/or any other contaminant, present in approximately the same proportion as found in vivo. For example, in some embodiments, the components are found in the same proportion as found in an intact cell. Because the methods provided herein allow nucleic acid or DNA to be bound to a solid support through the tagmentation process, other contaminants can be removed by washing the solid support after tagmentation occurs. The biological sample can comprise, for example, a crude cell lysate or whole cells. For example, a crude cell lysate that is applied to a solid support in a method set forth herein, need not have been subjected to one or more of the separation steps that are traditionally used to isolate nucleic acids from other cellular components.

Thus, in some embodiments, the biological sample can comprise not only purified nucleic acids from any source but also, for example, unpurified nucleic acids as found in blood, plasma, serum, lymph, mucus, sputum, urine, semen, cerebrospinal fluid, bronchial aspirate, feces, and macerated tissue, or a lysate thereof, or any other biological specimen comprising nucleic acid or DNA material. Target nucleic acid may be from a tissue sample, tumor sample, cancer cells, or a biopsy sample.

Target nucleic acid may come from any species, of from a mixture of species. For example, target nucleic acid may be from a mammal (such as a human, dog, cat, cow, pig, sheep, or other domesticated animal), or other species such as fish, bacteria, virus, fungus, or archaea. Nucleic acid may come from an environmental samples, such as soil or water.

In some embodiments, the target nucleic acid is DNA. In one such embodiment, the DNA is double-stranded. In some further embodiments, the double-stranded DNA comprises genomic DNA. In some other embodiments, the target nucleic acid is RNA or a derivative thereof, or cDNA.

In some embodiments, a biological sample (raw sample or extract) is processed to purify target nucleic acid prior to the tagmentation methods described herein. In some embodiments, the biological sample is a raw sample or a raw sample lysate (e.g., blood or saliva). In some embodiments, the treatment method comprises providing a raw sample, raw sample lysate, or pre-processed sample (e.g., a blood or saliva sample), mixing the sample with a lysis buffer and proteinase K, incubating the mixture to lyse cells in the sample and release DNA from the cells, thereby provided target nucleic acid(s) for the tagmentation methods described herein.

Components in raw samples or raw sample lysates such as blood, or additives in pre-processed samples such as saliva that has been collected in an Oragene collection tube (stabilization agents in collection tubes), may inhibit tagmentation reactions. Thus, provided herein is a method for treating a raw sample, raw sample lysate, or pre-processed sample to overcome this problem. In some embodiments, the method comprises providing a raw sample, raw sample lysate, or pre-processed sample (e.g., a blood or saliva sample), mixing the sample with a lysis buffer, proteinase K, and DNA purification beads (e.g., SPRI beads, beads comprising carboxyl groups, where the beads are optionally magnetic beads), incubating the mixture to lyse cells in the sample and release DNA from the cells, thereby capturing the DNA on the DNA purification or SPRI beads, and separating the beads comprising the captured DNA from the mixture. The separating serves to remove potential tagmentation inhibitors present in the supernatant. The method further comprises optionally washing the beads comprising the captured DNA, and eluting the DNA from the beads to provide target nucleic acid(s).

Methods of Sequencing

Some of the methods provided herein include methods of analyzing nucleic acids. Such methods include preparing a library of template nucleic acids of a target nucleic acid, obtaining sequence data from the library of template nucleic acids, and assembling a sequence representation of the target nucleic acid. In some embodiments, the methods described herein can be used in next-generation sequencing workflows including, but not limited to, sequencing by synthesis (SBS). Exemplary SBS procedures, fluidic systems, and detection platforms that can be readily adapted for use with nucleic acid libraries produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). The methods described herein are not limited to any particular type of sequencing instrumentation used.

EXAMPLES

The following examples serve to describe but not limit the disclosure provided herein.

Example 1: Tagmentation on a Solid Surface Using a Linker with Enzymatically Cleavable Nucleotides The transposons were formed by annealing two sets of oligonucleotides (represented as any one of SEQ ID NO: 9-11 (modified A14-ME) and any one of SEQ ID NO: 12-14 (modified B15-ME)), both of which base pair across a 19 base mosaic end (ME) sequence (SEQ ID NO: 8, shown in lower case letters) with a complementary mosaic end sequence (ME'; SEQ ID NO: 5). The oligonucleotides represented by SEQ ID NO: 9 through SEQ ID NO: 14 were 5' biotinylated to permit subsequent surface binding to streptavidin-coated paramagnetic beads. The annealed transposons were prepared by combining 50 µM of each biotinylated oligonucleotide with 50 µM of ME' (SEQ ID NO: 5) in the presence of 10 mM Tris-HCl (pH 8.0), 1 mM EDTA, and 25 mM NaCl and heated at 95° C. for 10 min, and cooling to room temperature for 2 hours. The annealed transposons were then mixed with a transposase enzyme at a final concentration of 2 µM and incubated at 37° C. overnight.

Examples of the cleavable linker sequences with cleavable nucleotide moieties are provided in SEQ ID NO: 9-14. The sequences labeled as SEQ ID NO: 9-14 comprise the 19 base mosaic end (ME) sequence (shown in lower case) and read 1 and read 2 sequences A14 and B15 (shown in italics). The sequences labeled as SEQ ID NO: 9 and SEQ ID NO: 12 comprise three uracil nucleotides (underlined) after a series of thymine residues (bolded). Similarly, the sequences labeled as SEQ ID NO: 10 and SEQ ID NO: 13 comprise three uracil nucleotides 3' of a series of thymine residues. SEQ ID NO: 11 and SEQ ID NO: 14 contain one uracil nucleotide after a series of thymine residues. As referenced herein, the thymine resides are part of the cleavable linker, and serve to connect the biotin to the cleavable moieties which are 5' of transposon and/or adaptor sequences. In some embodiments, the cleavable linker includes 1-10 cleavable uracil nucleotides. In some embodiments, the cleavable linker includes at least one cleavable uracil nucleotide. In some embodiment, the cleavable linker includes 2, 3, 4, 5, 6, 7, 8, 9, or 10 cleavable uracil nucleotides. SEQ ID NO: 8 is the 19 base mosaic end (ME) sequence and SEQ ID NO: 5 is its complement.

SEQ ID NO: 9
(modified A14-ME #1)
5'Biotin-TTTTTTTTTTUUUacac*TCGTCGGCAGCGTC*agatgtgtat aagagacag SEQ ID NO: 10
(modified A14-ME #2)
5'Biotin-TTUUU*TCGTCGGCAGCGTC*agatgtgtataagagacag SEQ ID NO: 11
(modified A14-ME #3)

-continued

5'Biotin-TTTTUTCGTCGGCAGCGTCagatgtgtataagagacag

SEQ ID NO: 12
(modified B15-ME #1)
5'Biotin-TTTTTTTTTTUUUGTCTCGTGGGCTCGGagatgtgtataag
agacag SEQ ID NO: 13
(modified B15-ME #2)
5'Biotin-TTUUUGTCTCGTGGGCTCGGagatgtgtataagagacag SEQ ID NO: 14
(modified B15-ME #3)
5'Biotin-TTTTUGTCTCGTGGGCTCGGagatgtgtataagagacag Once the transposomes are formed, the transposomes were affixed to streptavidin-coated beads. The beads were then washed with a diluted solution of transposomes in HT1 buffer (Illumina). HT1 contains high salt required for the biotin-streptavidin binding to the beads. Beads and transposomes were incubated whilst mixing on a mixer for 1 hr. Following mixing, beads were re-suspended in a storage buffer containing 15% glycerol and other buffering agents (e.g. Tris).

Next, tagmentation was performed. For example, a tagmentation solution was added to the sample containing the immobilized transposomes and incubated at 55° C. for about 15 minutes. The tagmentation reaction comprised DNA (e.g., about 50 pg to 5 µg of DNA) and a tagmentation buffer. In one example, the tagmentation buffer comprises components necessary for a tagmentation reaction to occur, for example a buffer comprising 10 mM Tris acetate (pH 7.6), 5 mM magnesium acetate, and 10% dimethylformamide, as described in U.S. Pat. Nos. 9,080,211, 9,085,801, and 9,115,396, each of which is incorporated by reference. An immobilized library of tagged DNA fragments was generated.

Example 2: PCR Amplification of Tagmented DNA and Enzymatic Cleavage

The streptavidin-coated capture beads that have tagmented DNA thereon, as described in Example 1, were washed (e.g., three times), using a wash buffer comprising 5% SDS, 100 mM Tris-HCl (pH7.5), 100 mM NaCl, and 0.1% Tween 20, thereby denaturing the transposase enzyme from the transposome complex. The supernatant was removed following the wash step via magnetic capture of the streptavidin-coated paramagnetic particles (e.g., beads) and the beads comprising the immobilized tagmented libraries were retained, and further washed using 100 mM Tris-HCl (pH 7.5), 100 mM NaCl, and 0.1% Tween 20.

Gap filling of DNA fragments (to fill the gaps between the 5' ends of the ME' sequences and the 3' ends of the fragments (see, e.g., FIG. 5B) was performed by adding, for example, NEM mix (NEXTERA Rapid Capture Kit, Illumina) and incubating at 72° C. for 3 min.

Target amplification via thermocycling was performed to amplify the tagmented DNA by methods known to a skilled artisan. In some examples, a solution of PCR reagents (e.g., a mastermix (for example, NEM mix (NEXTERA Rapid Capture Kit, Illumina) comprising minimally a PCR buffer, deoxy nucleotides, divalent cation, DNA polymerase) and additives required for efficient amplification was added to the beads and the tagmented DNA bound to the beads was amplified by thermal cycling (e.g., 10 thermal cycles).

The supernatant containing the amplified tagmented DNA was removed from the reaction chamber and transferred to a new reaction chamber (e.g., tube, well, etc.). The amplified fragment mixture was treated with one or more enzymes that cleave the bases in the cleavable linker. Any one of the number of known nucleotide backbone-breaking enzymes may be used to digest the off target products to prevent off target hybridization to the genome. Examples of suitable enzymes include, but not limited to, are Uracil DNA glycosylase (UDG, also referred to as UNG), formamidopyrimidine DNA glycosylase (Fpg), RNAseH, Endo IV, Endo VIII, Klenow, or apyrase.

The amplified tagmented DNA was purified using SPRI or Ampure XP beads (Beckman Coulter), the method of purification is not limiting to the present disclosure. The tagmented libraries can be enriched using a protocol as described in NEXTERA Rapid Capture enrichment protocol (Illumina) or any other target capture method. The enriched DNA library is now ready for sequencing.

Example 3: Read Enrichment Using Enzymatic Cleavage of a Cleavable Linker Containing Uracil Briefly, 50 ng of NA12878 genomic DNA (Coriell Institute) was used for each condition tested. As the control reaction, DNA was tagmented and libraries prepared and enriched following NEXTERA Rapid Capture Enrichment (Illumina) protocol, according to manufacturer's recommendations. Uracil-containing cleavable linkers SEQ ID NO: 9 and SEQ ID NO: 13 were used.

Briefly, each 50 µL reaction contained 5× Tagmentation buffer, 50 ng DNA, 5 µL of 250 nM of transposome-conjugated Dynal paramagnetic beads (Life Technologies) with cleavable uracil linkers described in SEQ ID NO: 9 and SEQ ID NO: 13. The reaction was incubated at 55° C. for 15 min followed by addition of 15 µL of Stop Tagment (ST) buffer and then was incubated at room temperature for an additional 5 min. Samples were placed on a magnet and supernatant was removed. The beads were re-suspended in 50 µL NEM (Illumina) and incubated at 72° C. for 5 min followed by cool down to 10° C. Samples were placed on a magnet, and the supernatant was removed and washed in HT2 wash buffer (Illumina).

PCR reactions were prepared by adding 40 µL of EPM, 10 µL each of index primers (e.g., P5'-index-A14' and P7'-index-B15') and water. PCR amplification was performed as follows: 72° C. for 3 min; 98° C. for 30 sec followed by 10 cycles of 98° C. for 10 sec; 65° C. for 30 sec; 72° C. for 60 sec. The PCR products were treated with 5 µL of the USER enzyme mix (1 U/µl—NEB part number M5505L) and incubated at 37° C. for 30 min followed by size selection, using SPRI-based (Solid Phase Reversible Immobilization) paramagnetic AMPure XP beads (Beckman Coulter catalog no A63880) according to manufacturer's recommendations. First, 100 µL of USER-treated PCR product was mixed with 55 µL water and 105 µL paramagnetic beads. The sample was left off magnet for 5 min, on magnet for 5 min, followed by removal of the supernatant into a second size selection (250 µL supernatant+30 µl paramagnetic beads). The beads were washed in 80% ethanol, air dried, and eluted in 25 µl RSB (Illumina).

Enrichment of the USER enzyme-treated, size-selected samples was performed using a TruSight One probe panel (Illumina) according to the NEXTERA Rapid Capture Enrichment kit's protocol as per manufacturer's recommendations (Illumina). The samples were sequenced on a HiSeq 2500 as per manufacturer's recommendations (Illumina).

TABLE 1

Read enrichment using enzymatic cleavage of a cleavable linker

| Condition Tested | Percent Read Enrichment |
|---|---|
| Solution based tagmentation and enrichment | 70.4 |
| Uracil linker (−enzyme) | 45.0 |
| Uracil linker (+enzyme) | 67.4 |

As shown in Table 1, practicing solution based tagmentation and enrichment (e.g., NEXTERA Rapid Capture) resulted in 70% read enrichment. Using transposomes affixed to beads via a uracil containing linker but without the enzymatic cleavage treatment, the % read enrichment was significantly less at 45%. However, when the uracils in the linker are cleaved via enzymatic treatment, the enrichment increased to 67% thereby recapturing enrichment to the level of non-immobilized, or solution based, tagmentation, and enrichment.

Example 4: 6-Plex and 12-Plex Exome Enrichment With and Without Enzymatic Cleavage of a Uracil Linker The following example demonstrates an exome enrichment experiment using a linker of 5 thymines (5T) compared to a linker of two thymines and 3 uracils (2T3U) without enzymatic cleavage and with enzymatic cleavage (2T3U+ENZ) compared to TruSeq Rapid Exome Kit (Illumina).

The experimental procedure was as described for Example 3 except 7.5 µL transposome immobilized beads was used and the gap fill step was omitted. Enrichment was performed using the TruSeq Rapid Exome kit (Illumina). Sequencing was performed on HiSeq 2500 according to manufacturer's recommendations (Illumina).

TABLE 2

Exome read enrichment using enzymatic cleavage of the linker

| | Percent Read Enrichment | |
|---|---|---|
| Condition Tested | 6-plex | 12-plex |
| Solution based tagmentation and enrichment | 60 | 63 |
| 5T linker (−enzyme mix) | 52 | 42 |
| 2T3U linker (−enzyme mix) | 45 | 36 |
| 2T3U linker (+Enzyme mix) | 63 | 56 |

As shown in Table 2, only the 2T3U linker with enzymatic cleavage showed comparable enrichment metrics to solution based NEXTERA using TruSeq Rapid Exome kit (Illumina) or standard surface based tagmentation with 5T residues.

Example 5: Comparison of 5' and 3' Biotinylated Adaptor Oligonucleotide Methods

Figure 5B:
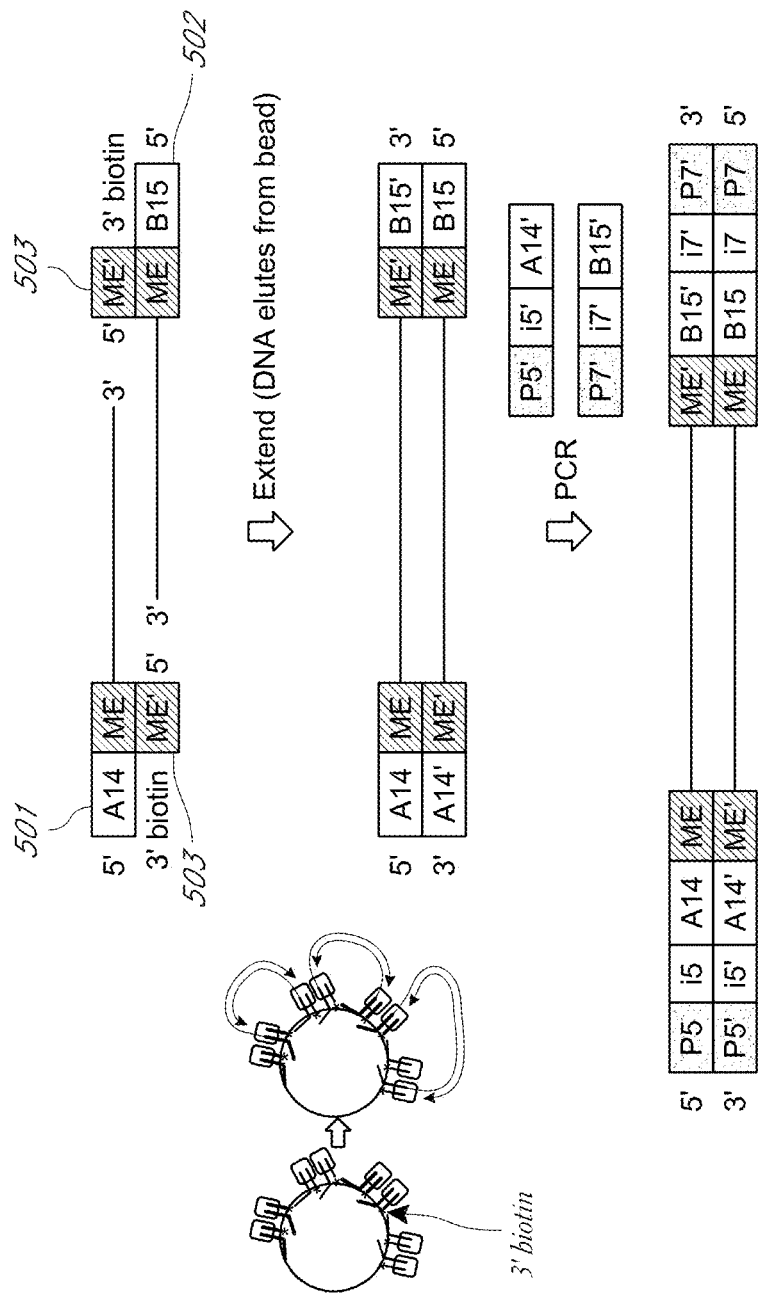
FIG. 5B shows an example of a biotinylated 3' end of a transposon sequence attached to a solid surface for tagmentation and subsequent amplification.

Certain bead-based tagmentation approaches use adaptor sequences that are biotinylated at the 5' end as shown in FIG. 5A. Briefly, the 5' biotinylated adaptor oligonucleotides 501 and 502 attach transposomes to the surface. The tagmentation event creates 5' biotinylated, fragmented whole genomic DNA that can contaminate a subsequent enrichment step. In one embodiment, the attachment of biotin is changed to a 3' position on the complementary strand (second transposon) to attach transposomes to the surface, as shown in FIG. 5B. Briefly, the oligonucleotides 501 and 502 are free of biotin. In this example, biotin is attached to the transposon end sequence 503 on the complementary strand (ME' sequence). In this configuration, the tagmentation event creates biotin-free genomic DNA fragments.

In yet another embodiment, a linker is between the 3' oligonucleotide 503 and the biotin. This can help reduce any steric hindrance for the transposition activity that might occur on the solid surface.

The following example demonstrates the use of 3' biotinylated oligonucleotide with a linker of Formula (I(a)) (glycerol-type linker) in preparation of sequencing libraries. As the control reaction, DNA was tagmented and libraries prepared and enriched following NEXTERA Rapid Capture Enrichment protocol, according to manufacturer's recommendations (Illumina). The experimental protocol described in Example 3 was followed except the tagmented, amplified DNA was enriched using the Xgen Lockdown hybridization capture kit protocol (Integrated DNA Technologies, IDT) using an Exome panel following manufacturer's recommended protocol. Foundationally, less than optimal enrichment was observed overall as sub-optimal blocking oligonucleotides were used as a substitute for the recommended universal blocking oligonucleotides supplied with the Xgen lockdown kit. However, the focus of the experiment does not require optimal blocking probes, just the ability to observe a measureable change in the focus of the experiment. The suboptimal blocking oligonucleotides are not expected to affect the focus of the experiment.

TABLE 3

Percent read enrichment for 3' biotinylated, 3'-spacer-biotin, 5' biotinylated adaptors compared to solution based tagmentation

| Test condition | Percent Read Enrichment |
|---|---|
| Solution-based tagmentation and enrichment | 37.5 |
| 3' biotin | 32.7 |
| 3' biotin with linker | 33.8 |
| 5' biotinyl with uracil linker + enzymatic cleavage | 9.2 |

As seen in Table 3, the 5' biotin with uracil linker+enzyme cleavage showed significantly lower enrichment compared to the control and the 3' biotin (with or without linker). The lower read enrichment with 5' biotin with uracil linker+Enzyme cleavage method may be the result of incomplete cleavage by the enzyme mix. Experiments with the 3' connection were shown to achieve comparable read enrichment to the solution-based control.

Example 6: Preparation of P Biotinylated Beads for Small Insert (150 to 200 bp)

Step 1. Anneal Transposons

A14-ME and B15-ME were each annealed to the ME'-Linker-Biotin oligo (preparation discussed below) resulting in two double-stranded complexes, both with the mosaic end (ME) specifically recognized by transposase and A14 or B15 sequence used in PCR to add secondary adapters. The A14-ME, B15-ME, and ME' oligos were resuspended to 200 nM. In a 96-well PCR plate, the preparations shown in Table 4 below were added in 2 wells (1 well for A14:ME' and 1 well for B15-ME'). The well plate was placed in a thermocycler for 10 min at 95° C., and then removed from the thermocycler and placed on a bench at room temperature for two hours.

TABLE 4

Preparation Conditions for the annealing reactions (50 μM)

| Annealing reaction | Top adaptor | ME' | 10xTEN | dH₂O | Total μL |
|---|---|---|---|---|---|
| A14: ME'-linker-biotin | 6.250 | 6.25 | 2.5 | 10.000 | 25 |
| B15: ME'-linker-biotin | 6.250 | 6.25 | 2.5 | 10.000 | 25 |

Step 2. Transposome Formation

The Tn5 transposase was added to the above annealed transposons forming a transposome complex containing the A14-ME/ME'-Linker-Biotin and B15-ME/ME'-Linker-Biotin complexes. The annealed oligos prepared from the previous step were used to set up the below reactions in a 96-well PCR plate. There was one well for A14-ME and one well for B15-ME. Each well was incubated in a thermocycler overnight at 37° C., providing two populations of transposome complexes; the contents of the two wells were then mixed together. After the mixing step, about 220 uL was removed and added into another well. About 220 uL of standard storage buffer (440 uL total) was added.

TABLE 5

Transposome Formation Conditions

| Transposon | μL | Std. Storage buffer | 50 μM Transposase EZ-Tn5 |
|---|---|---|---|
| A14: ME'-linker-biotin | 4.9 | 112.7 μL | 4.9 μL |
| B15: ME'-linker-biotin | 4.9 | 112.7 μL | 4.9 μL |

Step 3. Streptavidin Bead Loading

The above-formed transposome complexes containing a biotin linkage were added to streptavidin beads. The density of the complexes on the beads can be tuned to control insert size in the tagmentation products. The streptavidin beads were mixed well. About 200 uL of streptavidin beads was placed into a 1.5ml tube and placed on a tube magnet. The beads were washed twice with 1 mL HT1, and the beads were then re-suspend and spun down between washes. After the second wash, the beads were fully re-suspended with 600 uL of HT1. 400 uL of the above-made transposome complex was added to the tube with the HT1. The mixture was mixed on a rotary mixer for 1 hour and placed on a magnet, and the supernatant was removed. The mixture was re-suspend in 500 uL of 15% standard storage buffer. The beads were loaded in the presence of 1000 nM transposome complexes and the resulting 1000 nM density complexes were diluted to and stored at a concentration of 400 nM in solution. Thus, the stock solution included beads with a complex density of 1000 nM, diluted to 400 nM concentration. The dilution step does not change the density of the complexes on the beads, but only the final concentration of complexes in the stock solution.

Step 4. Tagmentation

A DNA sample was tagmented to make fragments by using the bead-loaded transposomes to cut and add the transposon sequence to the DNA samples. In a 96 well PCR plate, 5×Mg Tagmentation buffer (10 uL), DNA (>50 ng; 10 uL), dH₂O (20 uL), and transposome beads (prepared as in Step 3; 10 uL) were combined. The mixture was mixed well and incubated at 55° C. for 5 min followed by 2 min at 20° C. The tagmentation process was stopped by inactivating the transposase enzyme by treatment with SDS. 10 μL of SDS was added and mixed well with the reaction mixture from the step above. The mixture was then incubated at room temperature on the bench for 5 minutes and placed on magnetic stirrer. Once the solution turned clear, the supernatant was removed.

Step 5. Wash Stop Tagmentation

The SDS was washed away from the beads to prepare the sample for PCR. The reaction mixture, after the tagmentation was stopped, was removed from the magnet and 100 uL of wash buffer was added. The sample was vortexed for 20 sec at 1600 rpm. It was then placed on a magnetic stirrer again and once the solution turned clear, the supernatant was removed. The wash step was repeated for a total of three times. Once the wash was complete, all supernatant was removed and the sample was removed from the magnetic stirrer.

Step 6. PCR

The sample from Step 5 was PCR-amplified with primers that recognize A14 and B15 and added secondary adapters. The primers also include index sequences and sequencing primers (P5 and P7). The master mix shown in Table 6 was added to each sample well. The beads were re-suspended in the master mix, and placed in a thermocycler using the program shown in Table 7. This step served to remove the non-transferred/biotinylated strand, extend, and amplify to introduce P5 and P7 all in one process.

TABLE 6

PCR master mix

| | |
|---|---|
| i5 index for enrichment (E50X) - 20 μM | 10 μL |
| i7 index (N70X) -20 μM | 10 μL |
| dH₂O | 10 μL |
| Enhanced Polymerase Mix (EPM) (KAPA HiFi polymerase, dNPTs, buffer) | 20 μL |
| total | 50 μL |

TABLE 7

Thermocycler program

| |
|---|
| 72° C. 3 min |
| 98° C. 3 min |
| 98° C. 20 sec |
| 65° C. 30 sec (9 cycles) |
| 72° C. 1 min |
| repeat last 3 steps 8 more times (total 9 cycles) |
| 72° C. 3 mins |
| 10° C. hold |

The sample was removed from the thermocycler and placed on a magnetic stirrer. 45 μL of the sample was then transferred from the PCR plate to a MIDI plate. 77 uL of water was added to the MIDI plate samples and 88 μL of Ampure SPRI beads were added to each sample/water. The mixture was mixed well, incubated at room temperature for 5 minutes, and then placed on the magnetic stirrer. Once the solution turned clear, 200 μL of the sample was added to a new well on the same MIDI plate. 20 μL of Ampure SPRI beads were added, and the sample was mixed well and left at room temperature for 5 minutes. It was then placed on a magnetic stirrer again.

Once the solution turned clear, the supernatant was removed and discarded. The plate was left on the magnet stirrer and 200 μL of 80% ethanol was added without disturbing the pellet. The ethanol was later removed. The ethanol wash step was repeated for a total of two additional times. Once the wash was complete, any excess ethanol was removed with a pipet while the plate was on the stirrer. The sample was dried at room temperature for 5 minutes. 27 µl of water was added and mixed well. The sample was left at room temperature for 2 mins and placed back on the magnetic stirrer. 25 µl of the sample was transferred to a clean plate and stored at −20° C.

Example 7. A14-ME and B15-ME Transposons

A14-ME and B15-ME transposons were each annealed to ME' containing a 3' biotin. The 3' biotin was coupled to the ME' to form 3'-(I(a)) and 3'-(I(c)) linkers. The annealing reaction was in a 25 µL volume using a NaCl buffer. The resulting double-stranded transposons were each complexed with transposase in overnight reactions at 37° C. After the transposome complexes were formed, the A14 and B15 transposome complexes were mixed together in equal volumes and loaded onto streptavidin beads at a concentration of 300 nM to yield bound complexes at a density of 300 nM. Once attached to beads, the (I(a)) and (I(c)) 300 nM density mixtures were further diluted to a concentration of 120 nM. Thus, the beads still have a 300 nM density, but the complexes are present at a concentration of 120 nM in the diluted solution. The dilution step does not change the density of complexes on the beads, and therefore affects library yield but not insert size.

The resulting two types of bead-linked transposomes, 3'-(I(a)) and 3'-(I(c)), were stored at 25° C. for 28 and 56 days. Arrhenius equations estimates these to be accelerated to 4 (28 days) and 8 (56 days) months. After the accelerated age was finished, the two types of bead-linked transposomes were taken through tagmentation and library preparation steps as discussed above to assess the activity of the transposomes.

Figure 6A:
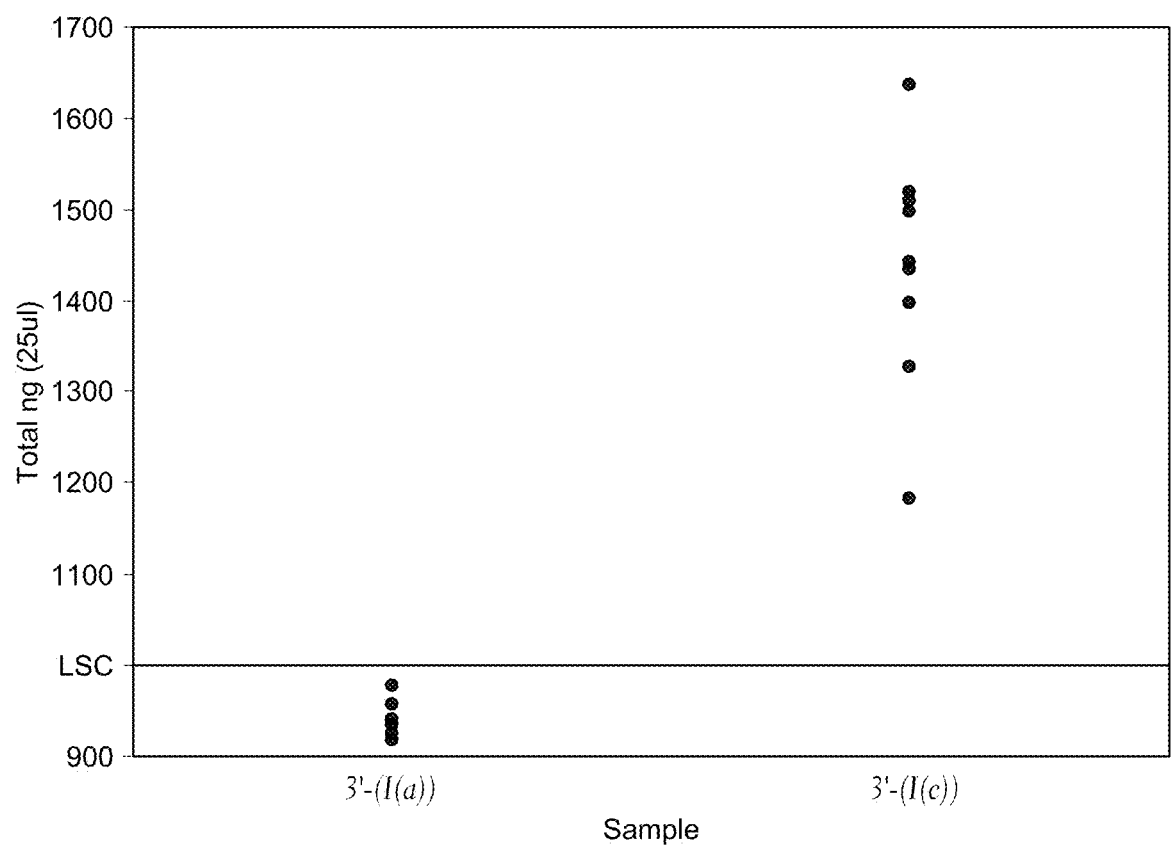
FIG. 6A compares the library yield from streptavidin bead-based solid-phase tagmentation using a transposome complexes having two different 3'-biotinylated linkers.

The bead-linked transposome complexes were added to gDNA along with a magnesium based buffer and placed at 55° C. for 5 minutes. Once complete, an SDS buffer was added to the reaction and the mixture was allowed to incubate at room temperature for 5 minutes. The mixture was then placed on a magnetic stirrer and washed three times with a NaCl and Tris buffer. After the washes, a PCR master mix with secondary adaptor carriers comprising index sequences was added to beads and fully re-suspended. The sample was then PCR amplified to create additional amplicons. After PCR, a SPRI cleanup was done to remove extra carriers. The samples were run on a BioAnalyzer to measure activity (yield of library preparation method). As shown in FIG. 6A, the library yields from streptavidin bead-based solid-phase tagmentation using transposome complexes having the 3'-biotinylated linker of Formula (I(a)) (3'-(I(a)); glycerol linker) and Formula (I(c)) (3'-(I(c)); hexyl linker) were compared. Linker 3'-(I(c)) provided significant library yield. Linker 3'-(I(a)) provided a lower yield, but still a sequenceable yield. The LSC line in the figure was an arbitrary lower specification limit.

Figure 6B:
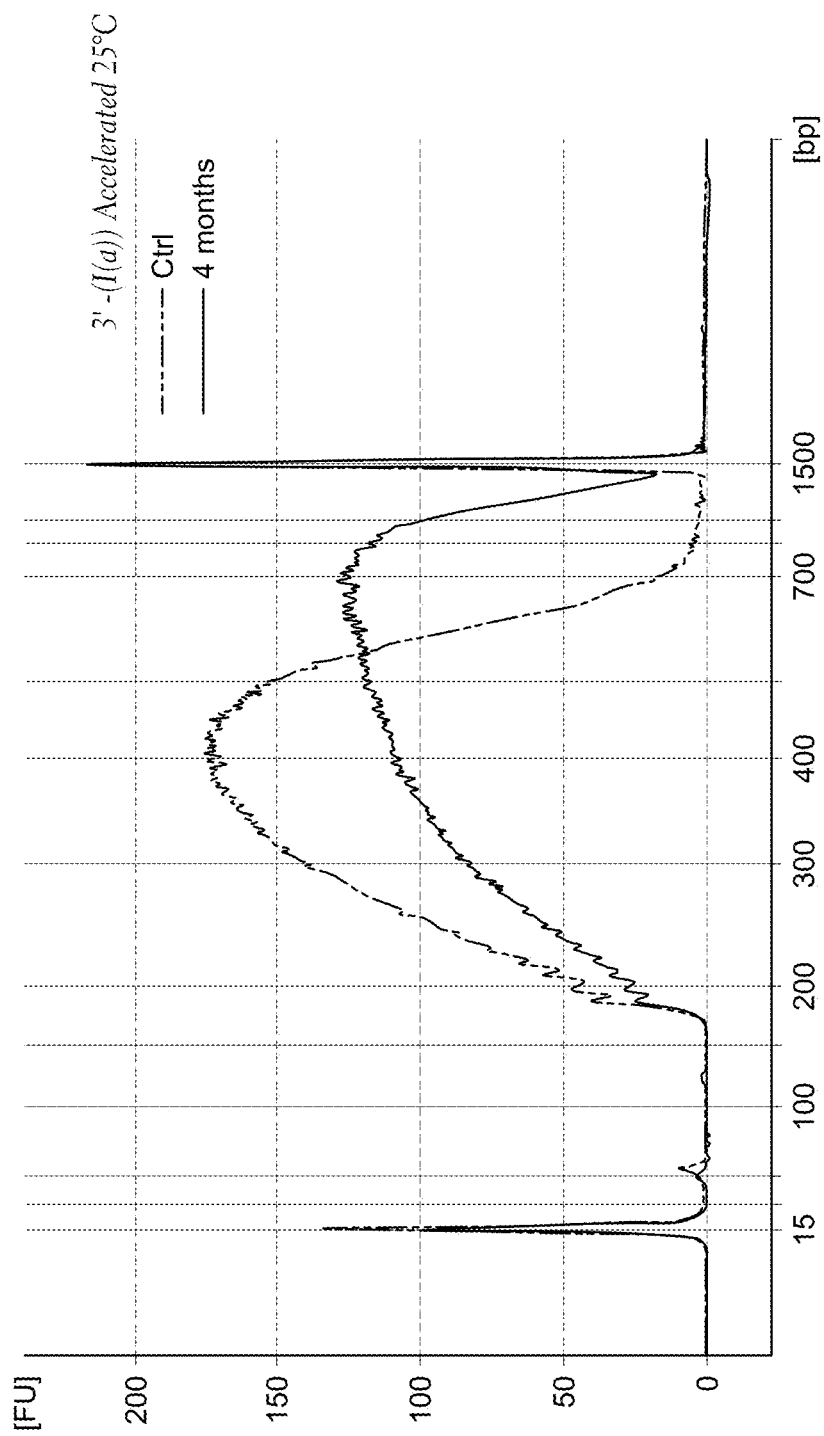
FIG. 6B demonstrates the accelerated stability data of the sample library prepared from streptavidin bead-based solid-phase tagmentation using a transposome complex having a 3'-biotinylated linker of Formula (I(a)) after aging for 4 months, compared to a sample library prepared from a non-aged batch of the same complex (control).
Figure 6C:
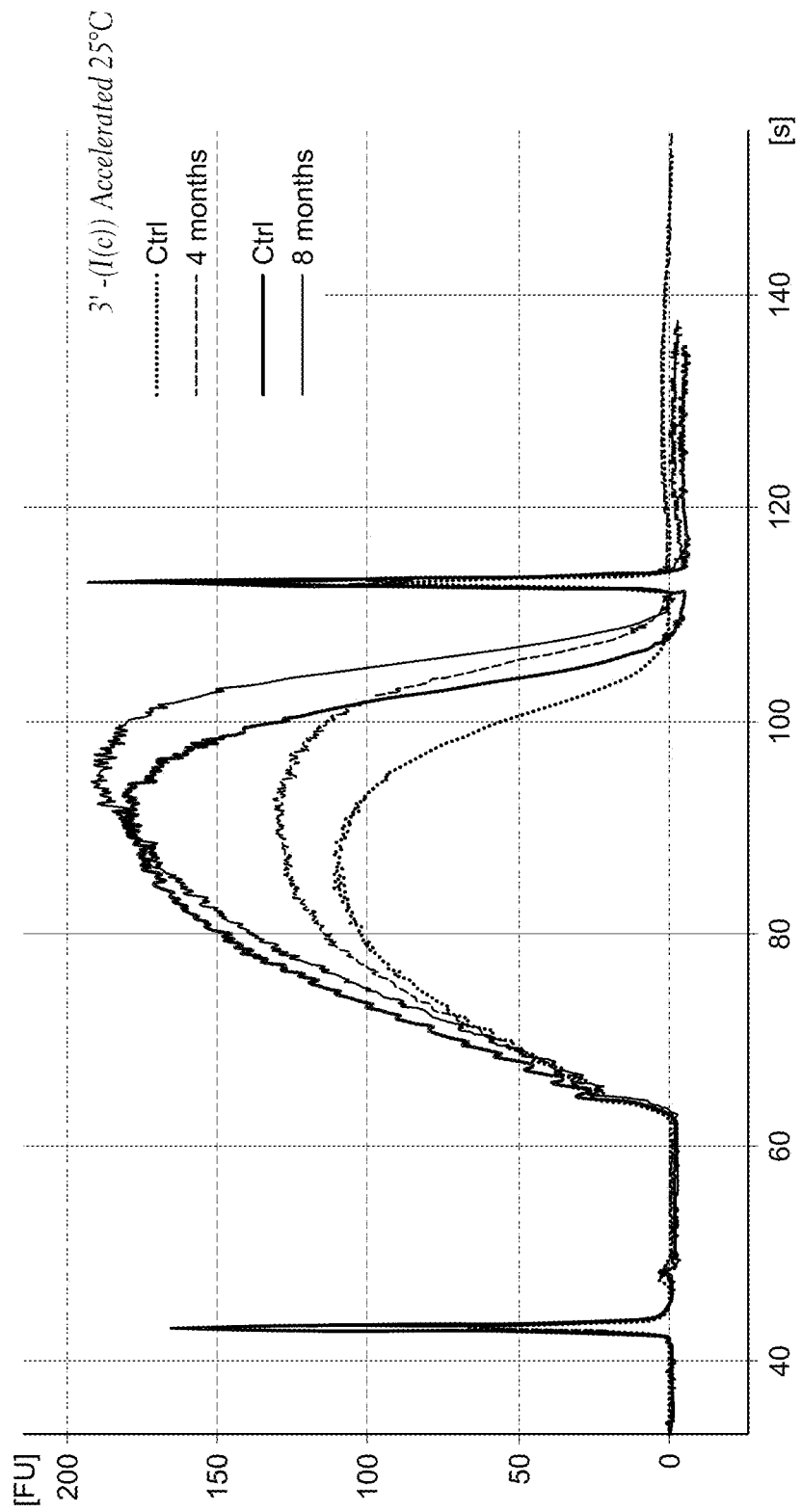
FIG. 6C demonstrates the accelerated stability data of the sample library prepared from a transposome complex having a 3'-biotinylated linker of Formula (I(c)) after aging for 4 months and 8 months, compared to sample libraries prepared from non-aged complexes (controls).

FIG. 6B illustrates the accelerated stability data of the sample library prepared from streptavidin bead-based solid-phase tagmentation using a transposome complex having the 3'-(I(a)) linker after aging for 4 months (accelerated storing condition at 25° C. for 28 days), compared to a sample library prepared from a non-aged control of the same linker at 4° C. for 28 days. FIG. 6C shows the accelerated stability data of the sample library prepared from a transposome complex having the 3'-(I(c)) linker after aging for 4 months and 8 months (accelerated storing condition at 25° C. for 28 days and 56 days), compared to sample libraries prepared from non-aged controls of the same linker at 4° C. for 28 days and 56 days respectively.

Example 8. A14-ME and B15-ME Transposons

A14-ME and B15-ME transposons were each annealed to ME' containing a 3' biotin. The 3' biotin was coupled to the ME' through the 3'-(I(c)) linker. The annealing reaction was in a 25 µl volume using a NaCl buffer. The resulting double stranded transposons were each attached to transposase in overnight reactions at 37° C. After the transposomes were formed, the A14 and B15 transposome complexes were mixed together in equal volumes and loaded onto streptavidin beads at various densities (10 nM to 800 nM).

The bead-linked transposomes at various densities were added to gDNA along with a magnesium based buffer and placed at 55° C. for 5 minutes. Once complete, an SDS buffer was added to the reaction and incubated at room temperature for 5 minutes. Then the mixture was placed on a magnetic stirrer and washed three times with a NaCl and Tris buffer. After the washes, a PCR master mix with secondary adaptor carriers comprising index sequences was added to the beads and fully re-suspended. A PCR reaction was then run on the samples to amplify the fragments. After PCR, a SPRI size selection was done at various SPRI ratios resulting in different insert sizes. The samples were run on a BA and a HiSeq 2500 Rapid Output to measure activity.

FIG. 7A shows the target insert size of DNA molecules as a function of the bead density using the streptavidin bead-based solid-phase library preparation where the beads comprises immobilized transposome complex bounded thereto through 3'-(I(c)). FIG. 7B shows the target insert size of the DNA molecules as a function of SPRI condition using streptavidin beads with an immobilized transposome complex comprising a hyperactive Tn5 transposase and the 3'-(I(c)) linker, with a complex density of 100 nM; and FIG. 7C shows the target insert size of the DNA molecules as a function of SPRI condition using streptavidin beads with immobilized transposome complex comprising a hyperactive Tn5 transposase and the 3'-(I(c)) linker, with a complex density of 600 nM.

Example 9. Integrated Extraction Protocol for Blood and Saliva

Fresh whole blood was processed using the Flex Lysis Reagent kit (Illumina, cat. no. 20015884). Fresh whole blood was collected into EDTA collection tubes and stored at 4° C. before processing. A lysis master mix was prepared by mixing the following volumes for each sample: 7 µl of Blood Lysis Buffer, 2 µl of proteinase K, and 31 µl of nuclease-free water. For each sample, 10 µl of blood, 40 µl of the lysis master mix, and 20 µl of SPRI beads was added to one well of a 96-well PCR plate and mixed by pipetting the solution 10 times. The plate was sealed and incubated for 10 minutes at 56° C. on a thermal cycler with a heated lid. The plate was then placed on a plate magnet for 5 minutes, the supernatant was discarded, and 150 µl of 80% ethanol was added. After incubation for 30 seconds on the magnet, the ethanol was discarded, and the plate was removed from the magnet. The beads were resuspended in 30 µl of water and ready for library preparation.

Saliva was collected in Oragene DNA Saliva Collection tubes (DNA Genotek, cat. nos. OGR-500, OGD-510), which were incubated for at least 1 hour at 50° C. to lyse the cells before thorough mixing by vortexing. For each sample, 20 µl of water and 30 µl of saliva was added to one well of a 96-well PCR plate and slowly mixed by pipetting. Then 20 µl of SPRI beads was added to the sample well and the beads were thoroughly mixed by pipetting the solution 10 times. The plate was incubated for 5 minutes at room temperature before being placed on a plate magnet for 5 minutes. The supernatant was removed and 150 µl of 80% ethanol was added to the bead pellet. The plate was then allowed to stand for 30 seconds on the magnet before removal of the ethanol and then removal of the plate from the magnet. The beads were resuspended in 30 µl of water and ready for library preparation.

A number of embodiments have been described. Nevertheless, it will be understood that various modifications may be made. Accordingly, other embodiments are within the scope of the following claims.

What is claimed is:

1. A transposome complex comprising:
   (i) a transposase,
   (ii) a first transposon comprising:
      (a) a 3' portion comprising a first transposon end sequence; and
      (b) a first adaptor sequence at the 5' end of the first transposon end sequence;
   (iii) a second transposon comprising a second transposon end sequence complementary to at least a portion of the first transposon end sequence; and
   (iv) a non-nucleic acid linker having a first end attached to the 3' end of the second transposon and a second end attached to an affinity element.

2. The complex of claim 1, wherein the linker and affinity element have the structure of Formula (I):

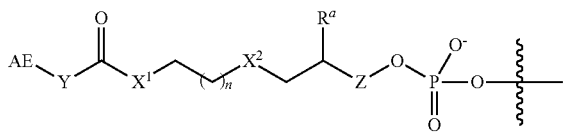

(I)

wherein:
AE is the affinity element;
Y is $C_{2-6}$alkylene;
$X^1$ is O, NW, or S;
   wherein $R^1$ is H or $C_{1-10}$ alkyl;
n is an integer from 1 to 6;
$X^2$ is O, $CH_2$, or S;
$R^a$ is H or —OH; and
Z is absent when $R^a$ is H, or is $CH_2$ when $R^a$ is H or OH;
   wherein the ⌇ marks the connection point to the second transposon.

3. The complex of claim 2, wherein the phosphate group in Formula (I) is connected to a 3' hydroxyl of the terminal nucleotide of the second transposon.

4. The complex of claim 2, wherein AE comprises or is an optionally substituted biotin or an amino group.

5. The complex of claim 2, wherein the linker and affinity element have the structure of Formula (I'):

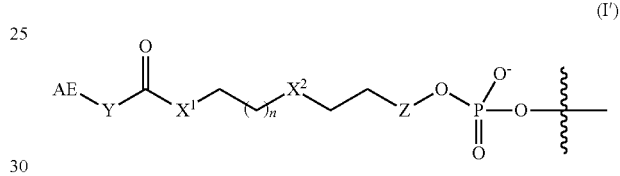

(I')

wherein Z is absent or is $CH_2$.

6. The complex of claim 2, wherein the linker and affinity element have the structure of Formula (Ia):

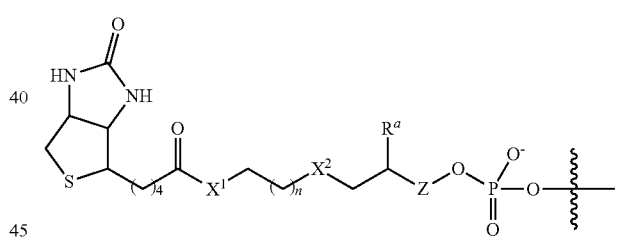

(Ia)

7. The complex of claim 2, wherein the linker and affinity element have the structure of Formula (Ib) or (Ic):

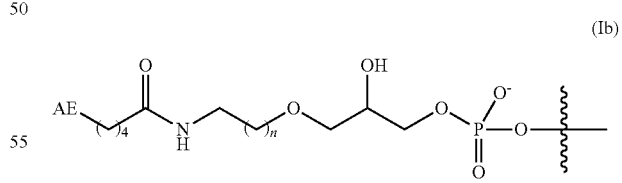

(Ib)

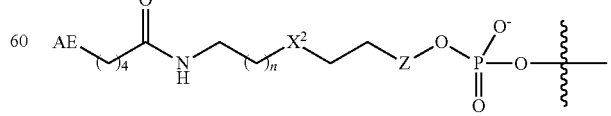

(Ic)

where n is 1 or 2;
$X^2$ is O or $CH_2$; and
Z is absent or is $CH_2$.

8. The complex of claim 2, wherein the linker and affinity element have a structure selected from the group consisting of:

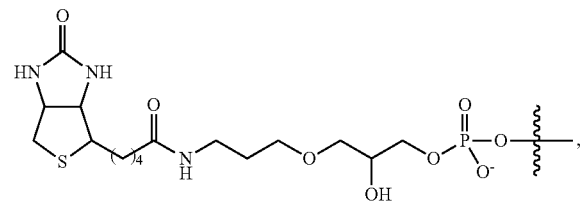
(I(a))

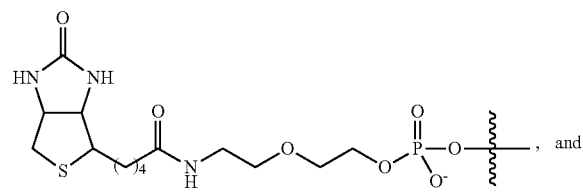
(I(b)), and

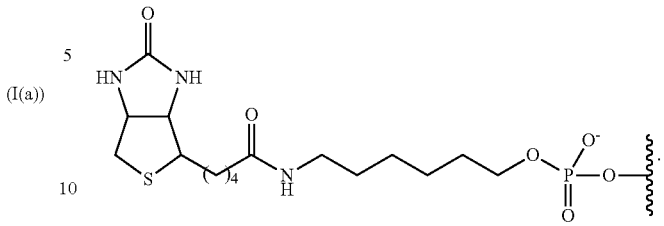
(I(c))

9. The complex of claim 1, wherein the transposase is a Tn5 transposase.

10. The complex of claim 9, wherein the first transposon end sequence and the second transposon end sequence are ME and ME'.

11. The complex of claim 1, wherein the first adaptor sequence comprises a primer sequence.

12. A first complex according to claim 11, wherein the first adaptor sequence comprises a first primer sequence, in a mixture comprising a second complex according to claim 11, wherein the first adaptor sequence of the second complex comprises a second primer sequence.

13. The complexes according to claim 12, wherein the first primer sequence comprises A14 and the second primer sequence comprises B15.

14. The complex of claim 1, wherein the affinity element is bound to an affinity binding partner on a solid support, whereby the complex is bound to the solid support.

15. The complex of claim 14, wherein the affinity element is biotin and the affinity binding partner is streptavidin.

* * * * *

UNITED STATES PATENT AND TRADEMARK OFFICE
CERTIFICATE OF CORRECTION

PATENT NO. : 10,920,219 B2
APPLICATION NO. : 15/900717
DATED : February 16, 2021
INVENTOR(S) : Grace DeSantis et al.

It is certified that error appears in the above-identified patent and that said Letters Patent is hereby corrected as shown below:

In Claim 2, Column 41, Line 53, delete "$X^1$ is O, NW, or S;" and insert --$X^1$ is O, $NR^1$, or S;--.

In Claim 6, Column 42, Lines 37-45, after the formula " 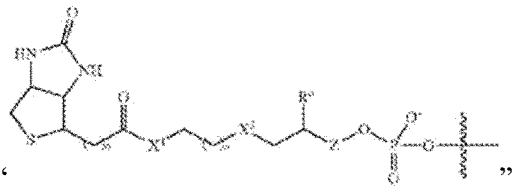 "
insert -- . --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*